(12) United States Patent
Ebersole et al.

(10) Patent No.: US 11,812,991 B2
(45) Date of Patent: Nov. 14, 2023

(54) SEAL ASSEMBLIES FOR SURGICAL ACCESS ASSEMBLIES

(71) Applicant: Covidien LP, Mansfield, MA (US)

(72) Inventors: Garrett Ebersole, Hamden, CT (US); Hari Naga Mahesh Kalepu, Hyderabad (IN); Raja Kamaraj, Hyderabad (IN); Sabastian George, Bangalore (IN); Dharani Gandhi, North Haven, CT (US)

(73) Assignee: Covidien LP, Mansfield, MA (US)

( * ) Notice: Subject to any disclaimer, the term of this patent is extended or adjusted under 35 U.S.C. 154(b) by 555 days.

(21) Appl. No.: 16/997,297

(22) Filed: Aug. 19, 2020

(65) Prior Publication Data

US 2021/0113240 A1    Apr. 22, 2021

Related U.S. Application Data

(60) Provisional application No. 62/916,931, filed on Oct. 18, 2019.

(51) Int. Cl.
*A61B 17/34* (2006.01)
*A61B 17/00* (2006.01)

(52) U.S. Cl.
CPC ...... *A61B 17/3462* (2013.01); *A61B 17/3423* (2013.01); *A61B 17/3498* (2013.01);
(Continued)

(58) Field of Classification Search
CPC ............ A61B 17/3462; A61B 17/3498; A61B 17/3423; A61B 17/3415; A61B 2017/345–3452; A61M 29/00–2029/025
See application file for complete search history.

(56) References Cited

U.S. PATENT DOCUMENTS

| 3,402,710 A | 9/1968 | Paleschuck |
|---|---|---|
| 3,495,586 A | 2/1970 | Regenbogen |

(Continued)

FOREIGN PATENT DOCUMENTS

| CA | 2702419 A1 | 11/2010 |
|---|---|---|
| CN | 202313634 U | 7/2012 |

(Continued)

*Primary Examiner* — Darwin P Erezo
*Assistant Examiner* — Brigid K Byrd
(74) *Attorney, Agent, or Firm* — Carter, DeLuca & Farrell LLP

(57) ABSTRACT

Access assemblies include an instrument valve housing and a valve assembly disposed within the instrument valve housing. The valve assembly includes a guard assembly, and a seal assembly disposed adjacent the guard assembly. The seal assembly includes a plurality of seal segments defining a substantially hexagonal body. Each seal segment of the plurality of seal segments includes a base portion and a seal portion extending from the base portion. Each base portion including an outer edge formed of three segments. Each seal segment of the plurality of seal segments is disposed relative to an adjacent seal segment of the plurality of seal segments such that two of the three segments of the outer edge of the respective seal segments align with each other. The valve assembly also includes a centering mechanism for biasing the seal assembly and guard assembly towards a center of the cavity of the instrument valve.

18 Claims, 23 Drawing Sheets

(52) U.S. Cl.
CPC .............. *A61B 2017/00862* (2013.01); *A61B 2017/3425* (2013.01); *A61B 2017/3486* (2013.01)

(56) References Cited

U.S. PATENT DOCUMENTS

| | | |
|---|---|---|
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,619,643 A | 10/1986 | Bai |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,271,380 A | 12/1993 | Riek et al. |
| 5,290,245 A | 3/1994 | Dennis |
| 5,290,249 A | 3/1994 | Foster et al. |
| 5,308,336 A | 5/1994 | Hart et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,334,150 A | 8/1994 | Kaali |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,346,459 A | 9/1994 | Allen |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,380,291 A | 1/1995 | Kaali |
| 5,385,552 A | 1/1995 | Haber et al. |
| 5,385,553 A | 1/1995 | Hart et al. |
| 5,391,156 A | 2/1995 | Hildwein et al. |
| 5,394,863 A | 3/1995 | Sanford et al. |
| 5,395,367 A | 3/1995 | Wilk |
| 5,407,433 A | 4/1995 | Loomas |
| 5,431,151 A | 7/1995 | Riek et al. |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,610 A | 5/1996 | Giglio et al. |
| 5,520,698 A | 5/1996 | Koh |
| 5,522,791 A | 6/1996 | Leyva |
| 5,524,501 A | 6/1996 | Patterson et al. |
| 5,524,644 A | 6/1996 | Crook |
| 5,538,509 A | 7/1996 | Dunlap et al. |
| 5,540,648 A | 7/1996 | Yoon |
| 5,545,150 A | 8/1996 | Danks et al. |
| 5,545,179 A | 8/1996 | Williamson, IV |
| 5,549,565 A | 8/1996 | Ryan et al. |
| 5,551,947 A | 9/1996 | Kaali |
| 5,556,385 A | 9/1996 | Andersen |
| 5,569,159 A | 10/1996 | Anderson et al. |
| 5,569,205 A | 10/1996 | Hart et al. |
| 5,569,291 A | 10/1996 | Privitera et al. |
| 5,569,292 A | 10/1996 | Scwemberger et al. |
| 5,577,993 A | 11/1996 | Zhu et al. |
| 5,591,192 A | 1/1997 | Privitera et al. |
| 5,601,581 A | 2/1997 | Fogarty et al. |
| 5,609,562 A | 3/1997 | Kaali |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,820 A | 11/1997 | Riek et al. |
| 5,685,857 A | 11/1997 | Negus et al. |
| 5,685,862 A | 11/1997 | Mahurkar |
| 5,697,946 A | 12/1997 | Hopper et al. |
| 5,709,671 A | 1/1998 | Stephens et al. |
| 5,709,675 A | 1/1998 | Williams |
| 5,713,858 A | 2/1998 | Heruth et al. |
| 5,713,869 A | 2/1998 | Morejon |
| 5,720,730 A | 2/1998 | Blake, III |
| 5,720,761 A | 2/1998 | Kaali |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,776,112 A | 7/1998 | Stephens et al. |
| 5,782,817 A | 7/1998 | Franzel et al. |
| 5,792,113 A | 8/1998 | Kramer et al. |
| 5,795,290 A | 8/1998 | Bridges |
| 5,800,451 A | 9/1998 | Buess et al. |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,471 A | 2/1999 | Ryan et al. |
| 5,871,474 A | 2/1999 | Hermann et al. |
| 5,876,413 A | 3/1999 | Fogarty et al. |
| 5,893,875 A | 4/1999 | O'Connor et al. |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,007,481 A | 12/1999 | Riek et al. |

(56) References Cited

U.S. PATENT DOCUMENTS

| | | |
|---|---|---|
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,093,176 A | 7/2000 | Dennis |
| 6,099,505 A | 8/2000 | Ryan et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,213,957 B1 | 4/2001 | Milliman et al. |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,355,028 B2 | 3/2002 | Castaneda et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,478,806 B2 | 11/2002 | McFarlane |
| 6,485,410 B1 | 11/2002 | Loy |
| 6,485,467 B1 | 11/2002 | Crook et al. |
| 6,487,806 B2 | 12/2002 | Murello et al. |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,551,282 B1 | 4/2003 | Exline et al. |
| 6,558,371 B2 | 5/2003 | Dorn |
| 6,562,022 B2 | 5/2003 | Hoste et al. |
| 6,569,120 B1 | 5/2003 | Green et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,038 B2 | 9/2003 | Bonutti et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,702,787 B2 | 3/2004 | Racenet et al. |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,736,797 B1 | 5/2004 | Larsen et al. |
| 6,740,064 B1 | 5/2004 | Sorrentino et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,835,201 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,855,128 B2 | 2/2005 | Swenson |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,942,671 B1 | 9/2005 | Smith |
| 6,945,932 B1 | 9/2005 | Caldwell et al. |
| 6,958,037 B2 | 10/2005 | Ewers et al. |
| 6,960,164 B2 | 11/2005 | O'Heeron |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,300,448 B2 | 11/2007 | Criscuolo et al. |
| 7,316,699 B2 | 1/2008 | McFarlane |
| 7,320,694 B2 | 1/2008 | O'Heeron |
| 7,331,940 B2 | 2/2008 | Sommerich |
| 7,344,547 B2 | 3/2008 | Piskun |
| 7,370,694 B2 | 5/2008 | Shimizu et al. |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |

(56) References Cited

U.S. PATENT DOCUMENTS

| | | |
|---|---|---|
| 7,481,765 B2 | 1/2009 | Ewers et al. |
| 7,493,703 B2 | 2/2009 | Kim et al. |
| 7,494,481 B2 | 2/2009 | Moberg et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,678,046 B2 | 3/2010 | White et al. |
| 7,686,823 B2 | 3/2010 | Pingleton et al. |
| 7,704,207 B2 | 4/2010 | Albrecht et al. |
| 7,708,713 B2 | 5/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,744,569 B2 | 6/2010 | Smith |
| 7,753,901 B2 | 7/2010 | Piskun et al. |
| 7,758,500 B2 | 7/2010 | Boyd et al. |
| 7,758,603 B2 | 7/2010 | Taylor et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,794,644 B2 | 9/2010 | Taylor et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,655 B2 | 12/2010 | Pasqualucci |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,918,827 B2 | 4/2011 | Smith |
| 7,947,058 B2 | 5/2011 | Kahle et al. |
| 7,951,076 B2 | 5/2011 | Hart et al. |
| 7,955,257 B2 | 6/2011 | Frasier et al. |
| 7,955,313 B2 | 6/2011 | Boismier |
| 7,985,232 B2 | 7/2011 | Potter et al. |
| 7,998,068 B2 | 8/2011 | Bonadio et al. |
| 8,002,750 B2 | 8/2011 | Smith |
| 8,002,786 B2 | 8/2011 | Beckman et al. |
| 8,012,128 B2 | 9/2011 | Franer et al. |
| 8,021,296 B2 | 9/2011 | Bonadio et al. |
| 8,025,670 B2 | 9/2011 | Sharp et al. |
| 8,029,475 B2 | 10/2011 | Franer et al. |
| 8,038,652 B2 | 10/2011 | Morrison et al. |
| 8,052,653 B2 | 11/2011 | Gratwohl et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,092,431 B2 | 1/2012 | Lunn et al. |
| 8,105,234 B2 | 1/2012 | Ewers et al. |
| 8,109,873 B2 | 2/2012 | Albrecht et al. |
| 8,118,735 B2 | 2/2012 | Voegele |
| 8,128,590 B2 | 3/2012 | Albrecht et al. |
| 8,137,318 B2 | 3/2012 | Schweitzer et al. |
| 8,147,453 B2 | 4/2012 | Albrecht et al. |
| 8,152,828 B2 | 4/2012 | Taylor et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,206,411 B2 | 6/2012 | Thompson et al. |
| 8,241,209 B2 | 8/2012 | Shelton, IV et al. |
| 8,262,568 B2 | 9/2012 | Albrecht et al. |
| 8,267,952 B2 | 9/2012 | Kahle et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,398,666 B2 | 3/2013 | McFarlane |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 8,597,180 B2 | 12/2013 | Copeland et al. |
| 8,961,406 B2 | 2/2015 | Ortiz et al. |
| 10,022,149 B2 | 7/2018 | Holsten et al. |
| 10,568,660 B2 | 2/2020 | Zhou |
| 10,653,449 B2 | 5/2020 | Main et al. |
| 2001/0037053 A1 | 11/2001 | Bonadio et al. |
| 2002/0055714 A1 | 5/2002 | Rothschild |
| 2002/0091410 A1 | 7/2002 | Ben-David et al. |
| 2002/0173748 A1 | 11/2002 | McConnell et al. |
| 2003/0014076 A1 | 1/2003 | Mollenauer et al. |
| 2003/0093104 A1 | 5/2003 | Bonner et al. |
| 2003/0109853 A1 | 6/2003 | Harding et al. |
| 2003/0187376 A1 | 10/2003 | Rambo |
| 2003/0187397 A1 | 10/2003 | Vitali |
| 2003/0233115 A1 | 12/2003 | Eversull et al. |
| 2003/0236549 A1 | 12/2003 | Bonadio et al. |
| 2004/0006356 A1 | 1/2004 | Smith |
| 2004/0054353 A1 | 3/2004 | Taylor |
| 2004/0059297 A1 | 3/2004 | Racenet et al. |
| 2004/0073090 A1 | 4/2004 | Butler et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0186434 A1 | 9/2004 | Harding et al. |
| 2004/0204682 A1 | 10/2004 | Smith |
| 2004/0204734 A1 | 10/2004 | Wagner et al. |
| 2004/0215209 A1 | 10/2004 | Almond et al. |
| 2004/0267096 A1 | 12/2004 | Caldwell et al. |
| 2004/0267204 A1 | 12/2004 | Brustowicz |
| 2005/0010238 A1 | 1/2005 | Potter et al. |
| 2005/0020884 A1 | 1/2005 | Hart et al. |
| 2005/0033342 A1 | 2/2005 | Hart et al. |
| 2005/0070850 A1 | 3/2005 | Albrecht |
| 2005/0070851 A1 | 3/2005 | Thompson et al. |
| 2005/0070935 A1 | 3/2005 | Ortiz |
| 2005/0070946 A1 | 3/2005 | Franer et al. |
| 2005/0070947 A1 | 3/2005 | Franer et al. |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0192594 A1 | 9/2005 | Skakoon et al. |
| 2005/0203346 A1 | 9/2005 | Bonadio et al. |
| 2005/0209608 A1 | 9/2005 | O'Heeron |
| 2005/0212221 A1 | 9/2005 | Smith et al. |
| 2005/0222582 A1 | 10/2005 | Wenchell |
| 2005/0245876 A1 | 11/2005 | Khosravi et al. |
| 2005/0251092 A1 | 11/2005 | Howell et al. |
| 2005/0251190 A1 | 11/2005 | McFarlane |
| 2005/0277946 A1 | 12/2005 | Greenhalgh |
| 2006/0020281 A1 | 1/2006 | Smith |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0211992 A1 | 9/2006 | Prosek |
| 2006/0212063 A1 | 9/2006 | Wilk |
| 2006/0217665 A1 | 9/2006 | Prosek |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |

(56) References Cited

U.S. PATENT DOCUMENTS

| | | |
|---|---|---|
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2006/0276751 A1 | 12/2006 | Haberland et al. |
| 2007/0088277 A1 | 4/2007 | McGinley et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0239108 A1 | 10/2007 | Albrecht et al. |
| 2007/0255218 A1 | 11/2007 | Franer |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0051739 A1 | 2/2008 | McFarlane |
| 2008/0058723 A1 | 3/2008 | Lipchitz et al. |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0146884 A1 | 6/2008 | Beckman et al. |
| 2008/0161758 A1 | 7/2008 | Insignares |
| 2008/0161826 A1 | 7/2008 | Guiraudon |
| 2008/0177265 A1 | 7/2008 | Lechot |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0208222 A1 | 8/2008 | Beckman et al. |
| 2008/0249475 A1 | 10/2008 | Albrecht et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093835 A1 | 4/2009 | Heinrich et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0234293 A1 | 9/2009 | Albrecht et al. |
| 2009/0275880 A1 | 11/2009 | Pasqualucci |
| 2009/0326330 A1 | 12/2009 | Bonadio et al. |
| 2009/0326332 A1 | 12/2009 | Carter |
| 2010/0016800 A1 | 1/2010 | Rockrohr |
| 2010/0030155 A1 | 2/2010 | Gyrn et al. |
| 2010/0049138 A1 | 2/2010 | Smith et al. |
| 2010/0063450 A1 | 3/2010 | Smith et al. |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0222801 A1 | 9/2010 | Pingleton et al. |
| 2010/0228090 A1 | 9/2010 | Weisenburgh, II |
| 2010/0228094 A1 | 9/2010 | Ortiz et al. |
| 2010/0228096 A1 | 9/2010 | Weisenburgh, II et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0261975 A1 | 10/2010 | Huey et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0286706 A1 | 11/2010 | Judson |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0087159 A1 | 4/2011 | Parihar et al. |
| 2011/0087168 A1 | 4/2011 | Parihar et al. |
| 2011/0087169 A1 | 4/2011 | Parihar et al. |
| 2011/0118553 A1 | 5/2011 | Stopek |
| 2011/0118833 A1 | 5/2011 | Reichenbach et al. |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0190592 A1 | 8/2011 | Kahle et al. |
| 2011/0201891 A1 | 8/2011 | Smith et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251559 A1 | 10/2011 | Tal et al. |
| 2011/0251560 A1 | 10/2011 | Albrecht et al. |
| 2011/0251633 A1 | 10/2011 | Smith |
| 2011/0276002 A1 | 11/2011 | Bierman |
| 2011/0313250 A1 | 12/2011 | Kleyman |
| 2012/0010569 A1 | 1/2012 | Parihar |
| 2012/0041371 A1 | 2/2012 | Tal et al. |
| 2012/0059640 A1 | 3/2012 | Roy et al. |
| 2012/0065590 A1 | 3/2012 | Bierman et al. |
| 2012/0109064 A1 | 5/2012 | Fischvogt et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2012/0316596 A1 | 12/2012 | Taylor et al. |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |

(56) References Cited

U.S. PATENT DOCUMENTS

| | | |
|---|---|---|
| 2015/0025477 A1 | 1/2015 | Evans |
| 2015/0065808 A1 | 3/2015 | Van Wyk et al. |
| 2015/0223833 A1 | 8/2015 | Coffeen et al. |
| 2018/0021063 A1* | 1/2018 | Main ................. A61B 17/3474 604/167.01 |
| 2019/0059938 A1 | 2/2019 | Holsten |
| 2019/0059944 A1 | 2/2019 | Holsten |

FOREIGN PATENT DOCUMENTS

| | | | |
|---|---|---|---|
| CN | 108354638 A * | 8/2018 | ....... A61B 17/00234 |
| DE | 202008009527 U1 | 10/2008 | |
| EP | 0226026 A2 | 6/1987 | |
| EP | 0538060 A1 | 4/1993 | |
| EP | 0577400 A1 | 1/1994 | |
| EP | 0630660 A1 | 12/1994 | |
| EP | 0807416 A2 | 11/1997 | |
| EP | 0950376 A1 | 10/1999 | |
| EP | 1188415 A2 | 3/2002 | |
| EP | 1312318 A1 | 5/2003 | |
| EP | 1774918 A1 | 4/2007 | |
| EP | 1932485 A1 | 6/2008 | |
| EP | 1994896 A1 | 11/2008 | |
| EP | 2044889 A1 | 4/2009 | |
| EP | 2044897 A1 | 4/2009 | |
| EP | 2080494 A1 | 7/2009 | |
| EP | 2095781 A2 | 9/2009 | |
| EP | 2098182 A2 | 9/2009 | |
| EP | 2138117 A1 | 12/2009 | |
| EP | 2138118 A2 | 12/2009 | |
| EP | 2145593 A1 | 1/2010 | |
| EP | 2181657 A2 | 5/2010 | |
| EP | 2226025 A1 | 9/2010 | |
| EP | 2229900 A1 | 9/2010 | |
| EP | 2238924 A1 | 10/2010 | |
| EP | 2238925 A1 | 10/2010 | |
| EP | 2238926 A2 | 10/2010 | |
| EP | 2238933 A1 | 10/2010 | |
| EP | 2248478 A1 | 11/2010 | |
| EP | 2248482 A1 | 11/2010 | |
| EP | 2253283 A1 | 11/2010 | |
| EP | 2272450 A2 | 1/2011 | |
| EP | 2277464 A1 | 1/2011 | |
| EP | 2289438 A1 | 3/2011 | |
| EP | 2292165 | 3/2011 | |
| EP | 2343019 | 7/2011 | |
| EP | 3242615 A1 | 11/2017 | |
| GB | 2469083 | 4/2009 | |
| JP | 2001525693 A | 12/2001 | |
| JP | 2004532660 A | 10/2004 | |
| JP | 2006187603 A | 7/2006 | |
| JP | 2008289889 A | 12/2008 | |
| JP | 2009534124 A | 9/2009 | |
| JP | 2011515128 A | 5/2011 | |
| WO | 8401512 | 4/1984 | |
| WO | 9314801 | 8/1993 | |
| WO | 9404067 | 3/1994 | |
| WO | 9610963 | 4/1996 | |
| WO | 9636283 | 11/1996 | |
| WO | 9733520 | 9/1997 | |
| WO | 9742889 | 11/1997 | |
| WO | 9850093 A1 | 11/1998 | |
| WO | 9916368 | 4/1999 | |
| WO | 9922804 | 5/1999 | |
| WO | 9929250 | 6/1999 | |
| WO | 0032116 | 6/2000 | |
| WO | 0032120 | 6/2000 | |
| WO | 0054675 | 9/2000 | |
| WO | 0108581 | 2/2001 | |
| WO | 0149363 | 7/2001 | |
| WO | 0207611 | 1/2002 | |
| WO | 03034908 A2 | 5/2003 | |
| WO | 03071926 | 9/2003 | |
| WO | 03077726 | 9/2003 | |
| WO | 2004043275 | 5/2004 | |
| WO | 2004054456 | 7/2004 | |
| WO | 2004075741 | 9/2004 | |
| WO | 2004075930 | 9/2004 | |
| WO | 2005058409 | 6/2005 | |
| WO | 2006019723 | 2/2006 | |
| WO | 2006100658 A2 | 9/2006 | |
| WO | 2006110733 | 10/2006 | |
| WO | 2006118650 A1 | 11/2006 | |
| WO | 2007018458 | 2/2007 | |
| WO | 2007095703 | 8/2007 | |
| WO | 2007143200 | 12/2007 | |
| WO | 2008015566 A2 | 2/2008 | |
| WO | 2008042005 | 4/2008 | |
| WO | 2008077080 | 6/2008 | |
| WO | 2008093313 | 8/2008 | |
| WO | 2008103151 | 8/2008 | |
| WO | 2008121294 A1 | 10/2008 | |
| WO | 2008147644 | 12/2008 | |
| WO | 2009036343 | 3/2009 | |
| WO | 2010000047 | 1/2010 | |
| WO | 2010141409 | 12/2010 | |
| WO | 2010141673 | 12/2010 | |
| WO | 2012131746 A1 | 10/2012 | |
| WO | 2014052532 A1 | 4/2014 | |
| WO | 2014116889 A1 | 7/2014 | |
| WO | 2016186905 A1 | 11/2016 | |
| WO | 2018024101 A1 | 2/2018 | |

* cited by examiner

SEAL ASSEMBLIES FOR SURGICAL ACCESS ASSEMBLIES

CROSS-REFERENCE TO RELATED APPLICATION

This application claims the benefit of and priority to U.S. Provisional Patent Application Ser. No. 62/916,931, filed Oct. 18, 2019, the entire disclosure of which is incorporated by reference herein.

FIELD

The present disclosure relates to access assemblies for minimally invasive surgery, including seals. More particularly, the present disclosure relates to seals for surgical access assemblies.

BACKGROUND

In order to facilitate minimally invasive surgery, a working space must be created in the desired surgical space. An insufflation gas, typically $CO_2$, is introduced into the abdomen of the patient to create an inflated state called pneumoperitoneum. Access ports are utilized to allow the introduction of surgical instrumentation and endoscopes (or other visualization tools). These ports maintain the pressure for the pneumoperitoneum, as they have one or more seals that adapt to the surgical instrumentation. Typically, a "zero-seal" in the access port seals the port in the absence of a surgical instrument in the port, and an instrument seal seals around a surgical instrument that has been inserted through the access port.

The breadth of surgical instrumentation on the market today requires a robust seal capable adjusting to multiple sizes and withstanding multiple insertions of surgical instrumentation. Some of the instrumentation can include sharp edges that can tear or otherwise damage seals. Therefore, it would be beneficial to have an access assembly with improved seal durability.

SUMMARY

An access assembly with an improved seal durability is provided. The access assembly includes an instrument valve housing, and a valve assembly disposed within the cavity of the instrument valve housing. The instrument valve housing includes upper, lower, and inner housing sections and defines a cavity. The valve assembly includes a seal assembly, a guard assembly disposed adjacent to and configured for engagement with the seal assembly, and a centering mechanism for maintaining the seal assembly and guard assembly centered within the cavity of the instrument valve. The guard assembly includes a ring portion and a plurality of petals. The plurality of petals extend radially outwardly from the ring portion when the guard assembly is in an unfolded condition, and the plurality of petals extend radially inward when the guard assembly is in a folded condition.

In embodiments, the guard assembly includes first, second, third and fourth petals, each petal including a flap portion and a connector portion for joining the flap portion to the ring portion. Each flap portion may include a first flap section and a second flap section. Each of the first and second flap sections may define a groove therebetween. The first flap section of each petal of the plurality of petals may overlap the second flap section of the adjacent petal of the plurality of petals.

In embodiments, the ring portion defines a plurality of openings and each connector portion defines a plurality of openings. The flap portion of the first guard member may overlap the flap portion of the second guard member. The flap portion of the second guard member may overlap the flap portion of the third guard member. The flap portion of the third guard member may overlap the flap portion of the fourth guard member. The flap portion of the fourth guard member may overlap the flap portion of the first guard member.

The valve assembly may further include upper, lower retainer, and middle members. At least one of the upper or lower retainer members may include a plurality of pins configured to engage the ring portion of the guard assembly. The seal assembly may include an hourglass-shaped seal supported by upper and lower flange members. The middle retainer member may be received between the upper and lower flange members. The centering mechanism may include a bellows. The centering mechanism may include an annular ring and a plurality of spokes extending outwardly from the annular ring. Each spoke of the plurality of spokes may include a rib extending at least partially along a length of the spoke.

Another access assembly with an improved seal durability is provided. The access assembly includes an instrument valve housing, and a valve assembly disposed within the cavity of the instrument valve housing. The instrument valve housing includes upper, lower, and inner housing sections and defines a cavity. The valve assembly includes a guard assembly, a seal assembly disposed adjacent the guard assembly, and a centering mechanism for maintaining the seal assembly and guard assembly centered within the cavity of the instrument valve. The seal assembly includes a plurality of seal sections. Each seal section of the plurality of seal sections includes a substantially C-shaped base portion and a semi-conical seal portion. Each seal section of the plurality of seal sections is secured to at least one adjacent seal section. The plurality of seal sections extending outwardly in a planar manner when the seal assembly is in an unfolded condition and the plurality of seal sections are stacked on top of one another when the seal assembly is in a folded condition.

The valve assembly may further include upper and lower retainer members. At least one of the upper or lower retainer members may include a plurality of pins configured to engage the base portions of the seal assembly.

In embodiments, the guard assembly includes a ring portion and a plurality of petals. The plurality of petals may extend radially outwardly from the ring portion when the guard assembly is in an unfolded condition. The plurality of petals may extend radially inward when the guard assembly is in a folded condition. The guard assembly and the seal assembly may be received between the upper and lower retainer members.

The centering mechanism may include a bellows. The centering mechanism may include an annular ring and a plurality of spokes extending outwardly from the annular ring. Each of the plurality of spokes may include a rib extending at least partially along a length of the spoke.

Another access assembly with an improved seal durability is provided. The access assembly includes an instrument valve housing, and a valve assembly disposed within the cavity of the instrument valve housing. The instrument valve housing includes upper, lower, and inner housing sections and defines a cavity. The valve assembly includes a guard assembly, and a seal assembly disposed adjacent guard assembly. The seal assembly includes a plurality of seal sections. Each seal section of the plurality of seal sections includes a substantially C-shaped base portion supporting a seal portion. A rim portion extends about an outer edge of the each base portion. Each seal section is received within the rim portion of the adjacent seal section such that the plurality of seal sections are stacked on top of one another.

In embodiments, each of the seal portions defines a wedge-shaped opening. Each base portion may include a plurality of openings. A distance between the plurality of openings and the rim portion may increase in a clockwise direction. The valve assembly may further include a centering mechanism for maintaining the seal assembly and guard assembly centered within the cavity of the instrument valve.

The valve assembly may further includes upper and lower retainer members. At least one of the upper or lower retainer members may include a plurality of pins configured to engage the base portions of the seal assembly.

In embodiments, the guard assembly includes a ring portion and a plurality of petals. The plurality of petals may extend radially outwardly from the ring portion when the guard assembly is in an unfolded condition. The plurality of petals may extend radially inward when the guard assembly is in a folded condition. The guard assembly and the seal assembly may be received between the upper and lower retainer members.

In embodiments, the centering mechanism includes a bellows. The centering mechanism includes an annular ring and a plurality of spokes extending outwardly from the annular ring, each of the plurality of spokes including a bent portion in loaded engagement with the instrument valve housing. Each of the plurality of spokes may include a rib extending at least partially along a length of the spoke.

Another access assembly includes an instrument valve housing and a valve assembly disposed within a cavity of the instrument valve housing. The instrument valve housing includes upper, lower, and inner housing sections. The valve assembly includes a guard assembly, and a seal assembly disposed adjacent the guard assembly. The seal assembly includes a plurality of seal segments defining a substantially hexagonal body. Each seal segment of the plurality of seal segments includes a base portion and a seal portion extending from the base portion. Each base portion including an outer edge formed of three segments. Each seal segment of the plurality of seal segments is disposed relative to an adjacent seal segment of the plurality of seal segments such that two of the three segments of the outer edge of the respective seal segments align with each other. The valve assembly also includes a centering mechanism for biasing the seal assembly and guard assembly towards a center of the cavity of the instrument valve.

In embodiments, each seal segment of the plurality of seal segments is clocked sixty degrees (60°) relative to an adjacent seal segment of the plurality of seal segments. The seal portions of the plurality of seal segments may taper radially inward. The seal portions of the plurality of seal segments may define an opening. The opening may include a diameter from about 0.025" to about 0.100". The seal portions of the plurality of seal segments may form an angle from about 180° to about 275°. In one embodiment, the angle may be 210°. The plurality of seal segments may include six (6) seal segments.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
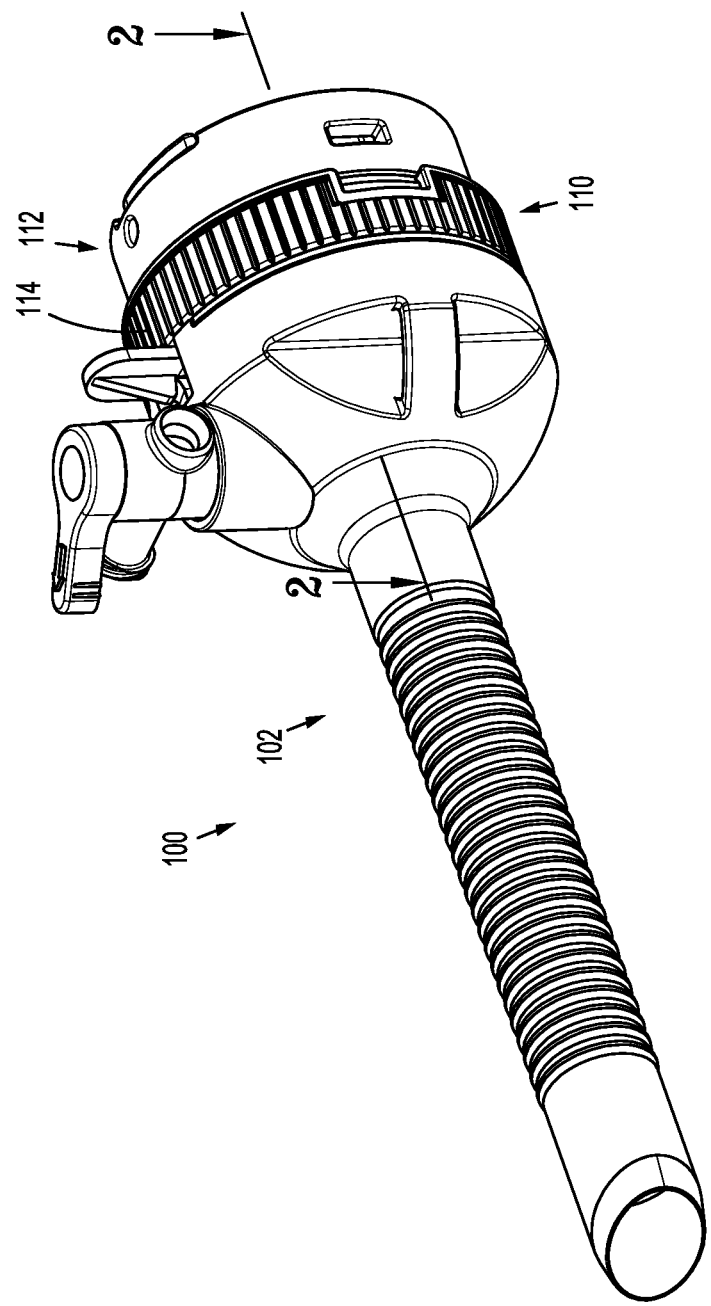
FIG. 1 is a perspective side view of an access port assembly according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Access port assemblies are employed during minimally invasive surgery, e.g., laparoscopic surgery, and provide for the sealed access of surgical instruments into an insufflated body cavity, such as the abdominal cavity. The access port assemblies of the present disclosure include an instrument valve housing mounted on a cannula tube, and include an obturator (not shown) inserted through the valve housing and cannula. The obturator can have a blunt distal end, or a bladed or non-bladed penetrating distal end and can be used to incise the abdominal wall so that the access port assembly can be introduced into the abdomen. The handle of the obturator can engage or selectively lock into the instrument valve housing of the access port assembly.

Access port assemblies are employed to tunnel through an anatomical structure, e.g., the abdominal wall, either by making a new passage through the structure or by passing through an existing opening through the structure. Once the trocar assembly has tunneled through the anatomical structure, the trocar obturator is removed, leaving the cannula assembly in place. The instrument valve housing of the cannula includes valves that prevent the escape of insufflation gases from the body cavity, while also allowing surgical instruments to be inserted into the cavity.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of an obturator. The bladeless obturator may be provided for the blunt dissection of the abdominal lining during a surgical procedure.

Various trocar obturators suitable for use with the cannulas of the present disclosure are known and include, for example, bladed, bladeless, blunt, optical, non-optical. For a detailed description of the structure and function of exemplary trocar assemblies, including exemplar trocar obturators and exemplar cannulas, please refer to commonly owned PCT Publication No. WO 2016/186905 ("the '905 publication"), the content of which is hereby incorporated by reference herein in its entirety.

With initial reference now to FIG. 1, an access port assembly according to aspects of the present disclosure is shown generally as cannula assembly 100. The cannula assembly 100 includes a cannula 102 and an instrument valve housing 110 secured to the cannula 102. For a detailed description of an exemplary cannula assembly, please refer to the '905 publication.

Figure 2:
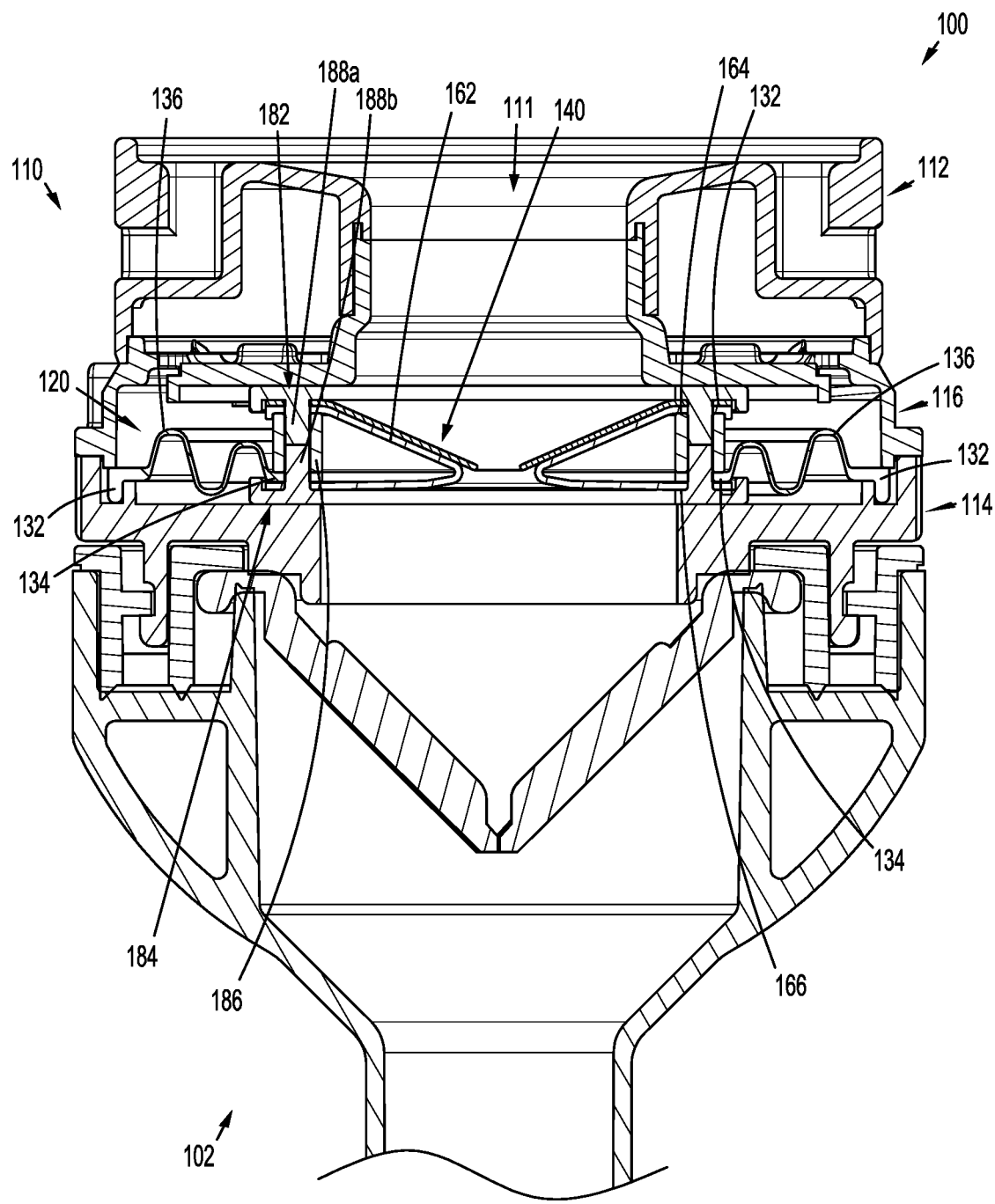
FIG. 2 a cross-sectional side view of the access port assembly shown in FIG. 1 taken along section line 2-2.

With reference to FIG. 2, the instrument valve housing 110 of the cannula assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing section 112, 114 of the instrument valve housing 110 may be selectively attachable to, and detachable from, the inner housing section 116. The lower housing section 114 may be releasably or permanently attached to a cannula tube 104 of the cannula assembly 102. In embodiments, either or both of the upper and lower housing sections 112, 114 of the instrument valve housing 110 may include knurls, indentations, tabs, or be otherwise configured to facilitate engagement by a clinician.

The cannula assembly 100 may also include features for the stabilization of the access port assembly. For example, the distal end of the cannula tube 104 can carry a balloon anchor or another expandable member that engages the abdomen from the interior side. For example, see commonly owned U.S. Pat. No. 7,300,448, the entire disclosure of which is hereby incorporated by reference herein. A feature on the opposite side of the abdominal wall can be used to further stabilize the access port assembly, such as adhesive tabs or adjustable foam collars.

The upper, lower, and inner housing sections 112, 114, 116 of the instrument valve housing 110 define a longitudinal passage 111 for receipt of a surgical instrument (not shown). The valve assembly 120 is supported within the instrument valve housing 110 to provide sealed passage of the surgical instrument through the cannula assembly 100.

Figure 3:
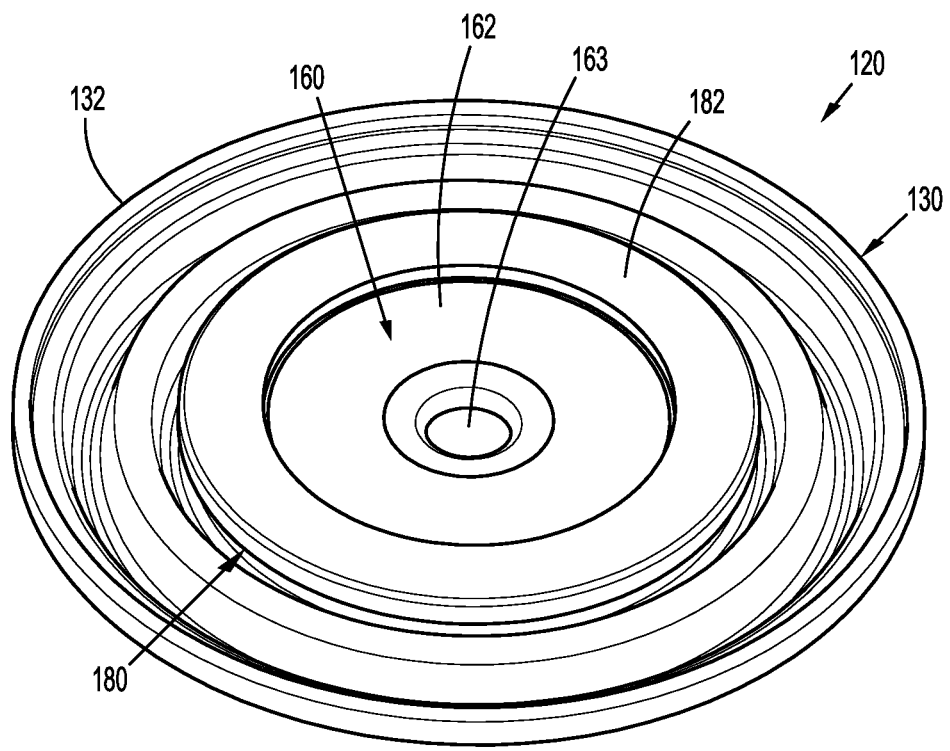
FIG. 3 is a perspective top view of a valve assembly of the access port assembly shown in FIG. 1.
Figure 4:
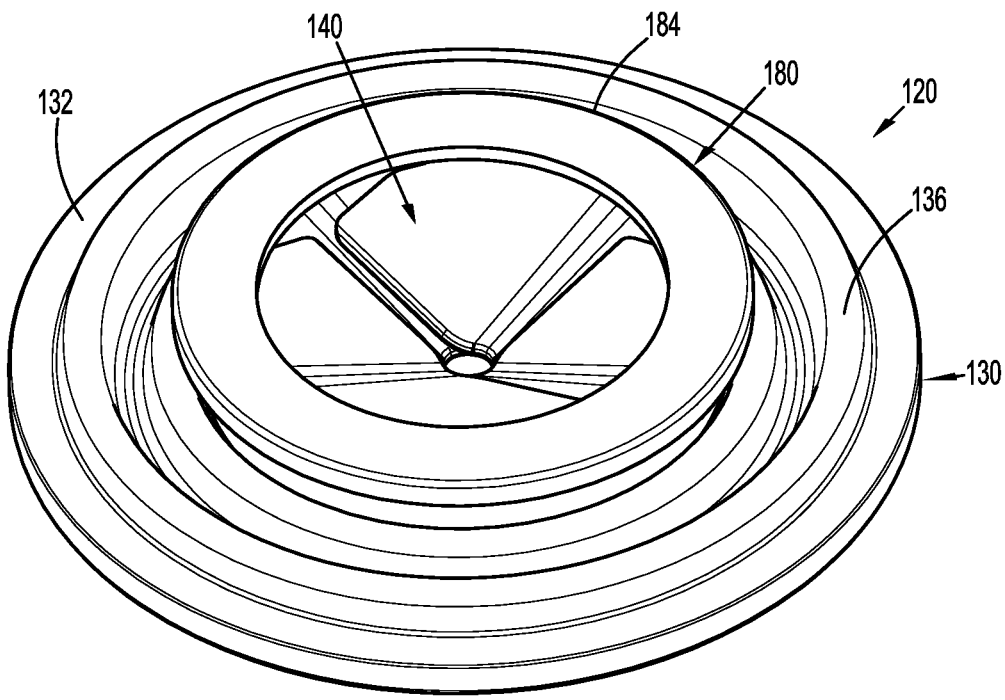
FIG. 4 is a perspective bottom view of the valve assembly shown in FIG. 3.
Figure 5:
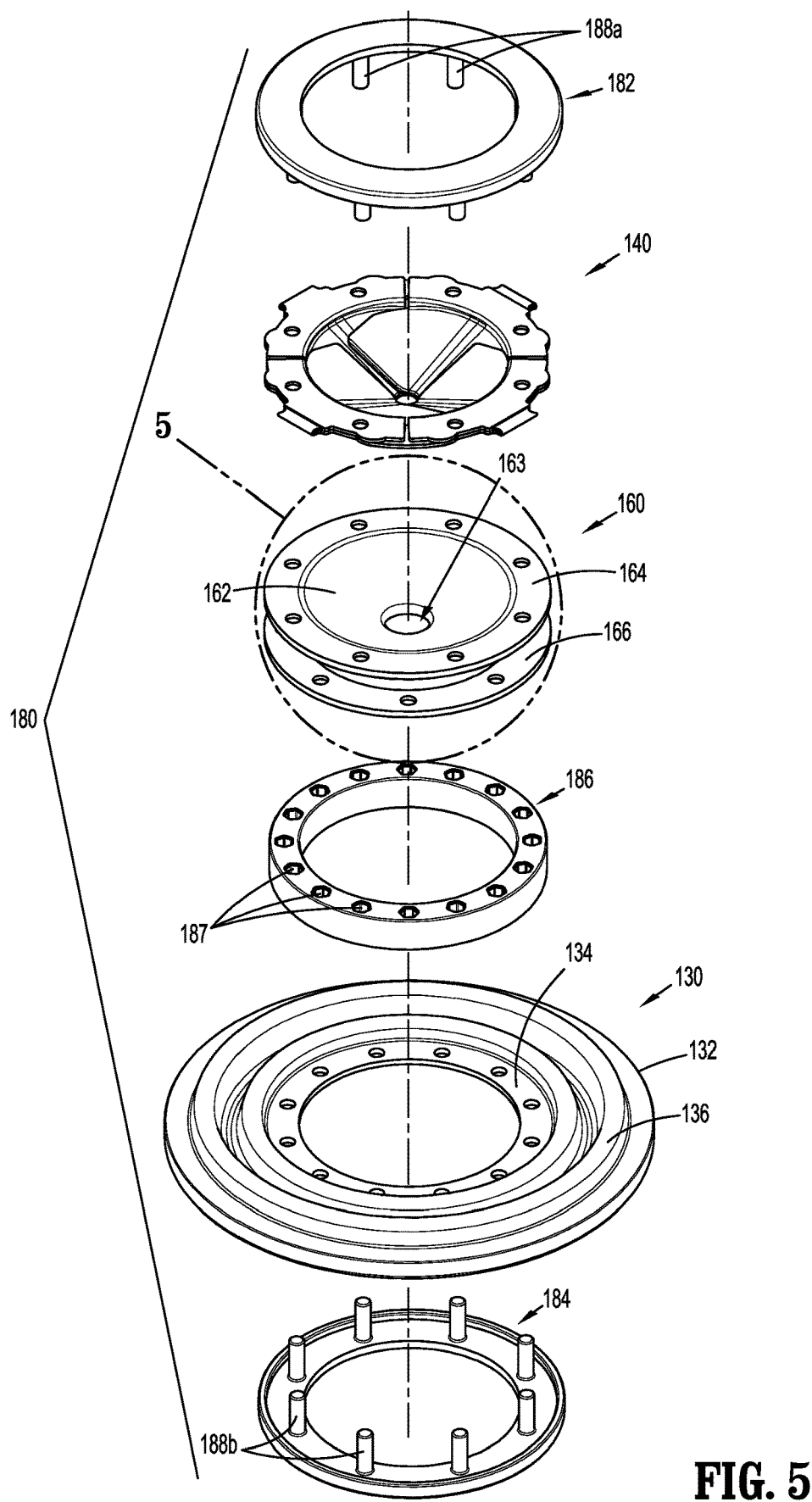
FIG. 5 is an exploded perspective view of the valve assembly shown in FIG. 3, including a centering mechanism, a guard assembly, a seal assembly, and a retainer assembly.

With particular reference to FIGS. 3-5, the valve assembly 120 supported in the instrument valve housing 110 includes a centering mechanism 130, a guard assembly 140, a seal assembly 160, and a retainer assembly 180. As will be described in further detail below, the centering mechanism 130 of the valve assembly 120 permits radial movement of the valve assembly 120 relative to the instrument valve housing 110 when a surgical instrument is received through the valve assembly 120, and returns the valve assembly 120 to a generally centered position once the surgical instrument is withdrawn from within the instrument valve housing 110. The guard assembly 140 protects the seal assembly 160 during insertion and withdrawal of a surgical instrument through the seal assembly 160. The seal assembly 160 provides sealed passage of the surgical instrument through the instrument valve housing 110. The retainer assembly 180 maintains the centering mechanism 130, the guard assembly 140, and the seal assembly 160 in an aligned relationship with one another.

With continued reference to FIGS. 2-5, as noted above, the centering mechanism 130 of the instrument valve housing 110 is configured to maintain the valve assembly 110 centered within the instrument valve housing 110 (FIG. 3). More particularly, the centering mechanism 130 includes an outer annular ring 132, an inner annular ring 134, and a bellows 136 disposed between the outer annular ring 132 and the inner annular ring 134. As shown in FIG. 2, the outer annular ring 132 is received between the inner housing section 116 and the lower housing section 114 to retain the centering mechanism 130 within the instrument valve housing 110. As will be described in further detail below, the inner annular ring 134 supports the seal assembly 160. For a detailed description of the structure and function of an exemplary centering mechanism, please refer to commonly owned U.S. Pat. No. 6,702,787 ("the '787 patent"), the content of which is incorporated herein by reference in its entirety.

Figure 6:
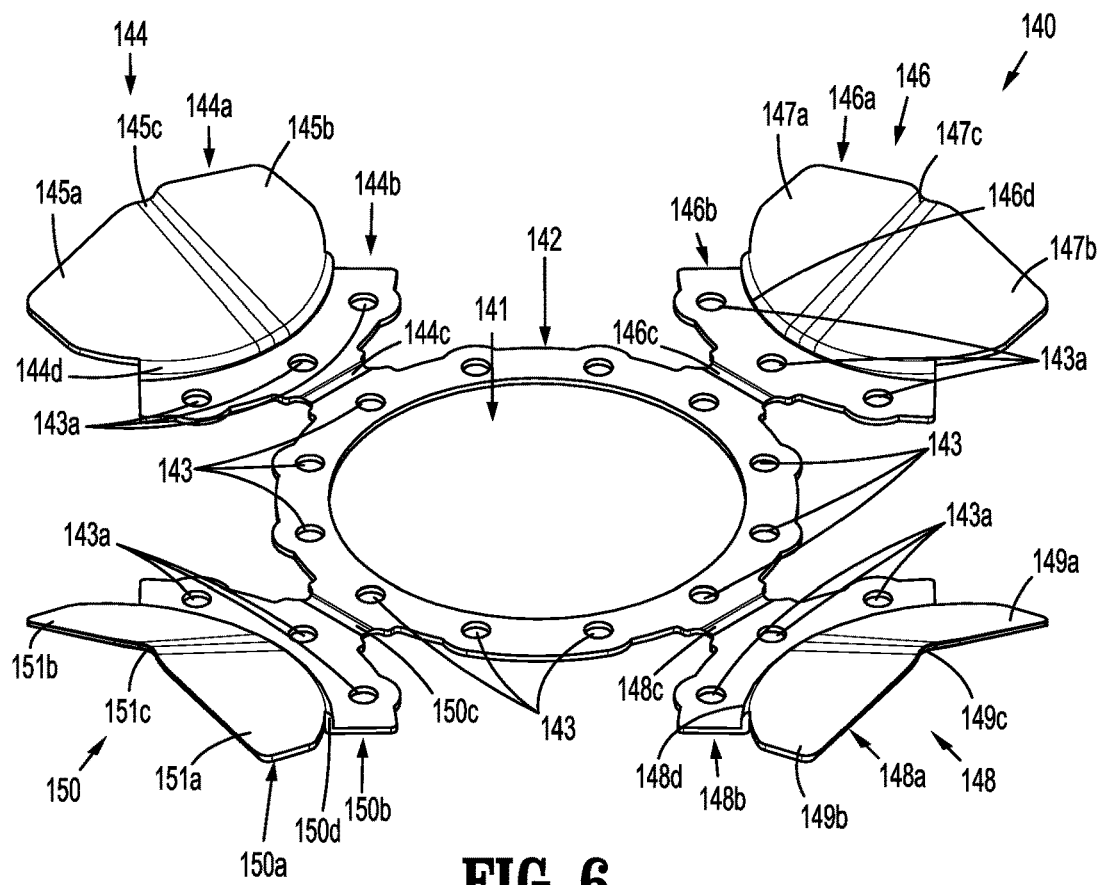
FIG. 6 is a perspective view of the guard assembly shown in FIG. 5, in an initial or unfolded condition.

With reference to FIG. 6, the guard assembly 140 of the valve assembly 120 includes a ring portion 142 and first, second, third, and fourth petals 144, 146, 148, 150 extending radially outward from the ring portion 142 when the guard assembly 140 is in an initial or unfolded condition. The guard assembly 140 may be formed from a sheet of plastic/polymeric material by stamping with a tool that forms the ring portion 142 and the petals 144, 146, 148, 150. In embodiments, the plurality of openings 143, 143a in the ring portion 142 and first, second, third, and fourth petals 144, 146, 148, 150 (described further below) may be formed in the same stamping or molding operation. Alternatively, the guard assembly 140 may be formed by molding or other techniques.

The ring portion 142 of the guard assembly 140 is configured to be received between an upper retainer member 182 of the retainer assembly 180 and the seal assembly 160. The ring portion 142 defines a central opening 141 for receipt of a surgical instrument (not shown) therethrough. The ring portion 142 of the guard assembly 140 further defines the plurality of openings 143. The plurality of openings 143 in the ring portion 142 facilitate engagement of the guard assembly 140 by the retainer assembly 180.

Each of the first, second, third, and fourth petals 144, 146, 148, 150 of the guard assembly 140 includes a flap portion 144a, 146a, 148a, 150a and a connector portion 144b, 146b, 148b, 150b supporting the respective flap portions 144a, 146a, 148a, 150a of the respective first, second, third, and fourth petals 144, 146, 148, 150 on the ring portion 142. In embodiments, and as shown, each of the first, second, third and fourth petals 144, 146, 148, 150 are secured to the ring portion 142 by a hinge portion 144c, 146c, 148c, 150c disposed between the respective connector portions 144b, 146b, 148b, 150b of the first, second, third, and fourth petals 144, 146, 148, 150 and the ring portion 142. The hinge portion 144c, 146c, 148c, 150c of the respective first, second, third, and fourth petals 144, 146, 148, 150 facilitate folding of the first, second, third, and fourth petals 144, 146, 148, 150 over the ring portion 142 of the guard assembly 140.

Each of the flap portions 144a, 146a, 148a, 150a of the respective first, second, third, and fourth petals 144, 146, 148, 150 of the guard assembly 140 includes first and second flap sections 145a, 145b, 147a, 147b, 149a, 149b, 151a, 151b, respectively, separated by a radial channel or groove 145c, 147c, 149c, 151c. Each of the first and second flap sections 145a, 145b, 147a, 147b, 149a, 149b, 151a, 151b of the respective flap portions 144a, 146a, 148a, 150a tapers radially inward and downward, i.e., away from the ring portion 142. The first and second flap sections 145a, 145b, 147a, 147b, 149a, 149b, 151a, 151b and the radial channels 145c, 147c, 149c, 151c operate as instrument guides directing a surgical instrument (not shown) through the flap portions 144a, 146a, 148a, 150a.

Each of the connector portions 144b, 146b, 148b, 150b of the first, second, third, and fourth petals 144, 146, 148, 150 defines a plurality of openings 143a. As will be described in further detail below, each of the plurality of openings 143a in the connector portions 144b, 146b, 148b, 150b of the respective first, second, third, and fourth petals 144, 146, 148, 150 align with the plurality of openings 143 in the ring portion 142 of the guard assembly 140 when the respective connector portions 144b, 146b, 148b, 150b are folded relative to the ring portion 142.

In embodiments, and as shown, the first, second, third, and fourth petals 144, 146, 148, 150 of the guard assembly 140 may each include a lip 144d, 146d, 148d, 150d, respectively, disposed between the flap portions 144a, 146a, 148a, 150a, respectively, and the respective connector portions 144b, 146b, 148b, 150b of the first, second, third, and fourth petals 144, 146, 148, 150. As shown in FIGS. 7-10, the lip 144d, 146d, 148d, 150d of the respective flap portions 144a, 146a, 148a, 150a recesses the flap portions 144a, 146a, 148a, 150a, respectively, within the central opening 141 of the ring portion 142 of the guard assembly 140. In this manner, the lips 144d, 146d, 148d, 150d are configured to reduce the cross-sectional profile, e.g., thickness, of the assembled guard assembly 140.

With particular reference to FIGS. 6-10, the guard assembly 140 of the valve assembly 120 is shown in sequential stages of folding. Referring initially to FIG. 6, the guard assembly 140 is shown in the initial, unfolded condition. In the initial condition, the first, second, third, and fourth petals 144, 146, 148, 150 of the guard assembly 140 extend radially outward from the ring portion 142 of the guard assembly 140. As noted above, the guard assembly 140 may be molded, stamped, or formed in any other suitable manner.

Figure 7:
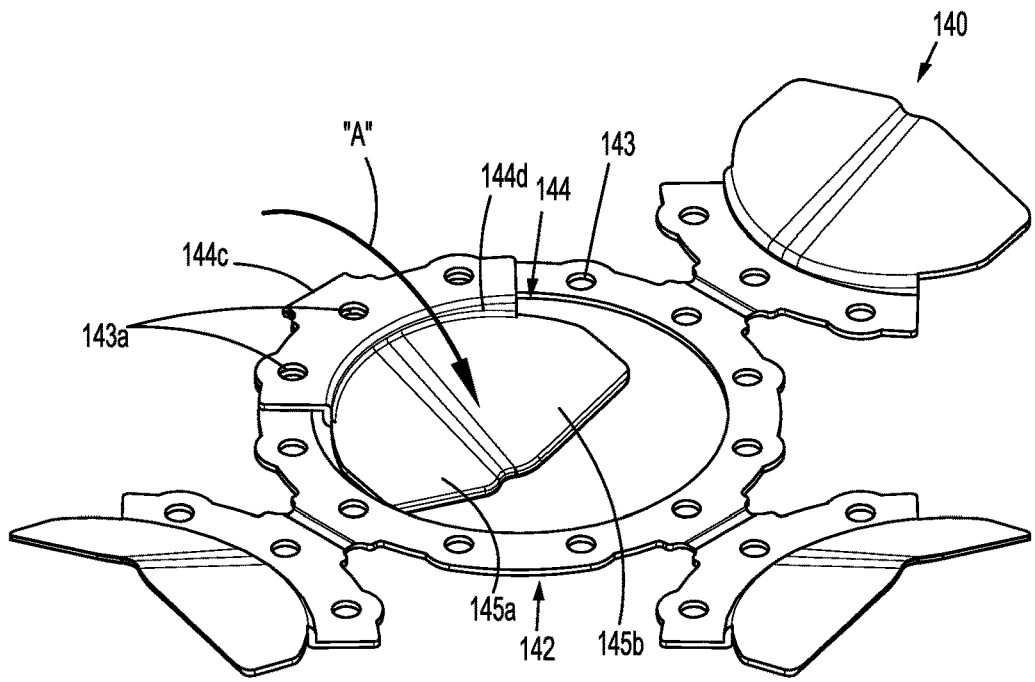
FIGS. 7-9 are perspective views of the guard assembly shown in FIG. 5, in sequential partially folded conditions.

Turning to FIG. 7, the first petal 144 of the guard assembly 140 is folded inwardly at the hinge portion 144c of the first petal 144 between the connection portion 144b of the first petal 144 and the ring portion 142 of the guard assembly 140, as indicated by arrow "A". The first petal 144 of the guard assembly 140 is folded such that the connector portion 144b of the first petal 144 overlaps the ring portion 142 of the guard assembly 140 and the plurality of openings 143a in the connector portion 144b align with the corresponding plurality of openings 143 in the ring portion 142 of the guard assembly. The lip 144d disposed between the flap portion 144a and the connector portion 144b of the first petal 144 recess the flap portion 144a within the central opening 141 of the ring portion 142 of the guard assembly 140.

Figure 8:
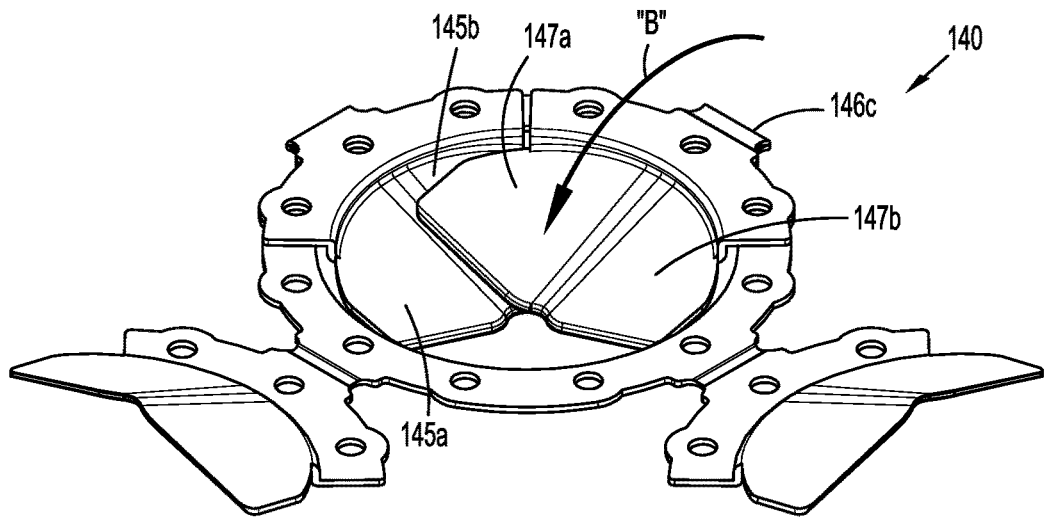
Figure 9:
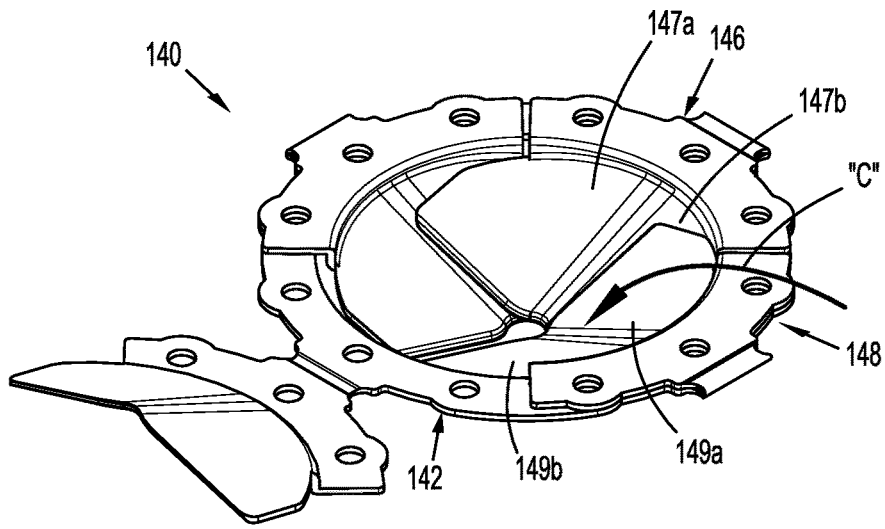
Figure 10:
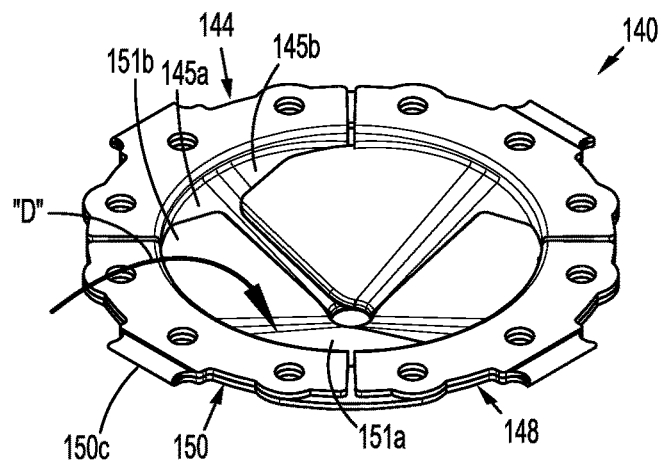
FIG. 10 is a perspective view of the guard assembly shown in FIG. 5, in a fully folded condition.

With reference to FIGS. 8-10, the guard assembly 140 with the second, third, and fourth petals 146, 148, 150 folded in the same manner as the first petal 144, in sequential order. More particularly, the second petal 146 is folded at the hinge portion 144d, as indicated by arrow "B" in FIG. 8, such that the first flap section 147a of the second petal 146 substantially covers the second flap section 145b of the first petal 146. The third petal 148 is folded at the hinge portion 148d, as indicated by arrow "C" in FIG. 9, such that the first flap section 149a of the third petal 148 substantially covers the second flap section 147b of the second petal 148. The fourth petal 150 is folded at the hinge portion 150d, as indicated by arrow "D" in FIG. 10, such that the first flap section 151a of the fourth petal 150 substantially covers the second flap section 149b of the third petal 148. The first flap section 145a of the first petal 144 is lifted to permit the second flap section 151b of the fourth petal 150 to be received under the first flap section 145a of the first petal 144 such that the first flap section 145a of the first petal 1444 substantially covers the second flap section 151b of the fourth petal 150. In this manner, the guard assembly 140 is folded such that each of the first flap sections 145a, 147a, 149a, 151a of the respective first, second, third, and fourth petals 144, 146, 148, 150 overlaps the adjacent second flap section 146b, 147b, 149b, 151b of the respective second, third, fourth, and first petals 146, 148, 150, 144.

The flap portions 144a, 146a, 148a, 150a of the respective first, second, third, and fourth petals 144, 146, 148, 150 of the guard assembly 140 are configured to flex downward upon engagement with a surgical instrument to facilitate passage of the surgical instrument through the seal assembly 160. More particularly, engagement of one or more of the flap portions 144a, 146a, 148a, 150a of the first, second, third, and fourth petals 144, 146, 148, 150, respectively, flexes one or more of the flap portions 144a, 146a, 148a, 150a downward into engagement with an hourglass-shaped seal 162 of the seal assembly 160 to stretch the hourglass-shaped seal 162 of the seal assembly 160 to increase the size of a central opening 163 of the hour-glass seal 162. The increased size of the central opening 163 of the hourglass-shaped seal 162 permits receipt of the surgical instrument through the valve assembly 120. The larger the diameter of the surgical instrument, the more the first, second, third, and fourth flap portions 144a, 146a, 148a, 150a of the respective first, second, third, and fourth petals 144, 146, 148, 150 are flexed downward, and the greater the size of the central opening 163 in the hour-glass seal 164. The flap portions 144a, 146a, 148a, 150a also operate to guide and orient the surgical instrument through the seal assembly 160.

In alternative embodiments, the third petal 148 of the guard assembly 140 may be folded prior to the second petal 146 is folded. In this manner, the first flap section 147a of the second petal 146 substantially covers the second flap section 145b of the first petal 144 and the second flap section 147b of the second petal 146 covers the first flap section 149a of the third petal 148. Similarly, and as noted above, the first flap section 151a of the fourth petal 150 substantially covers the second flap section 149b of the third petal 148 and the second flap section 151b of the fourth petal 150 substantially covers the first flap section 145a of the first petal 144.

It is envisioned that the guard assembly may include any number of petals, and the petals may include flap portions of any size or configuration. See U.S. Pat. Nos. 5,895,377 and 6,569,120, and PCT publication WO 91/12838, the entire disclosures of which are all hereby incorporated by reference herein, for exemplary guard assemblies, as well as other aspects of access port assemblies.

Figure 11:
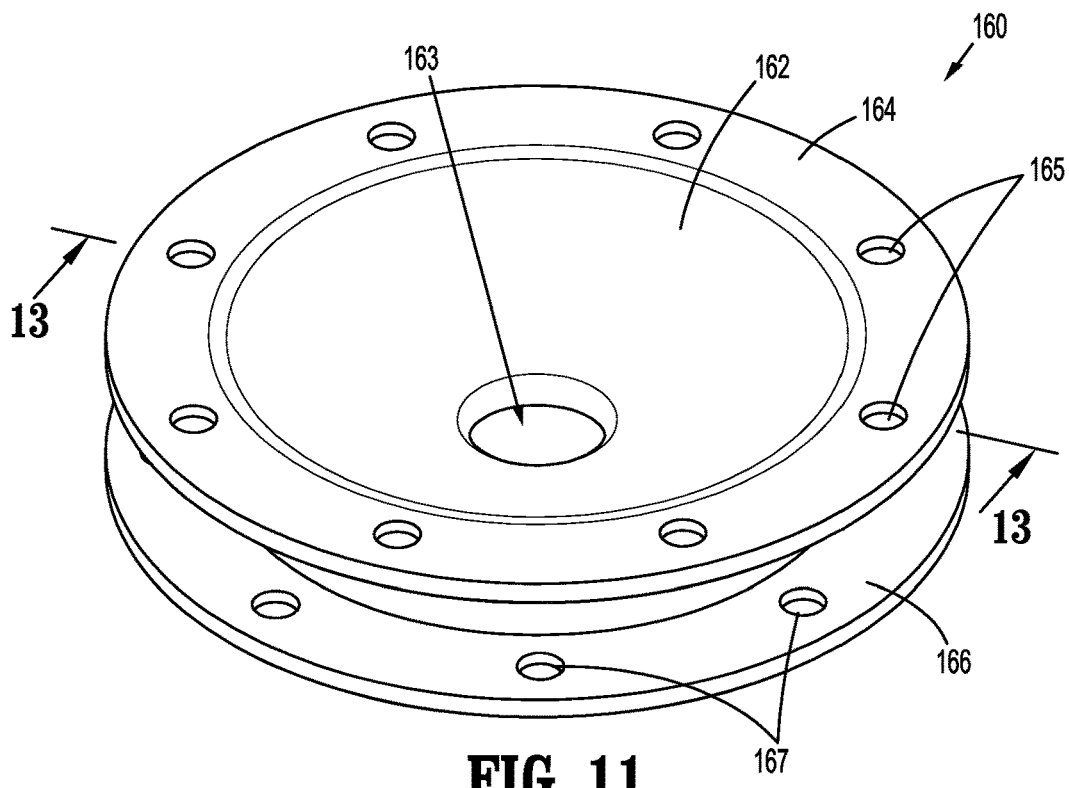
FIG. 11 is a perspective top view of the seal assembly shown in FIG. 5.
Figure 12:
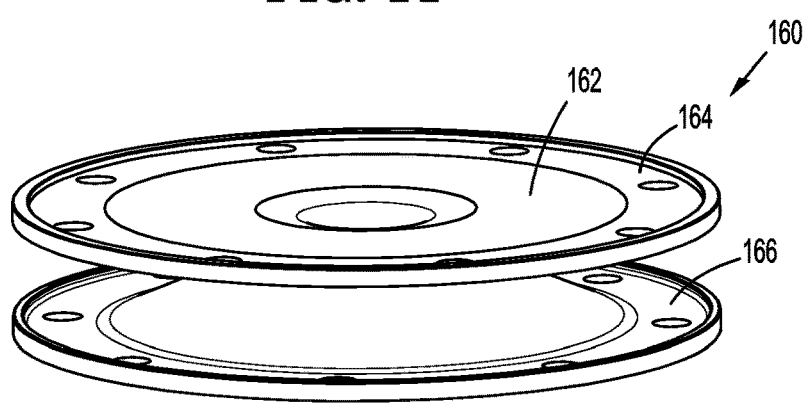
FIG. 12 is a perspective side view of the seal assembly shown in FIG. 11.
Figure 13:
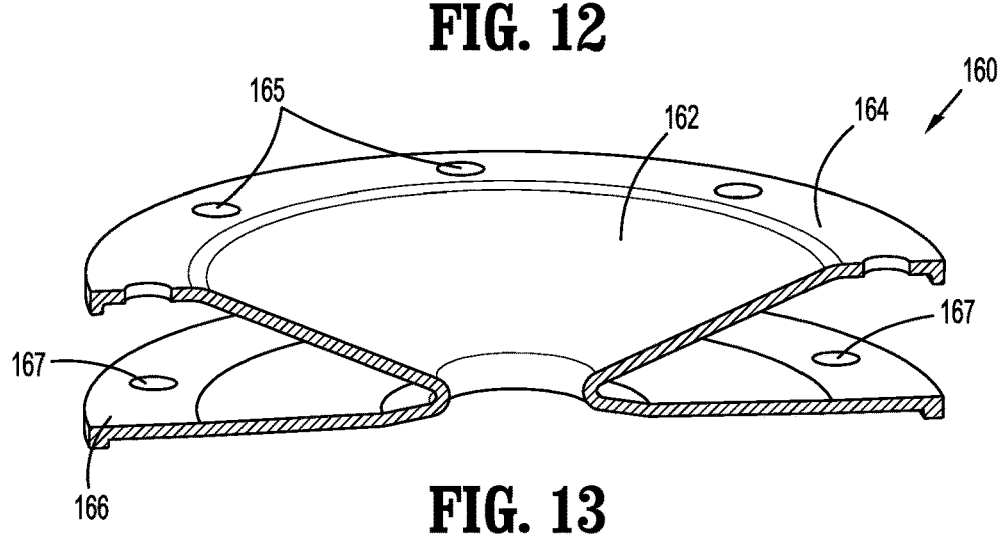
FIG. 13 is a cross-sectional side view of the seal assembly shown in FIG. 11 taken along section line 13-13.

Referring to FIGS. 11-13, the seal assembly 160 of the valve assembly 120 is configured to provide a seal around an outer surface of a surgical instrument (not shown) passing through the instrument valve housing 110 (FIG. 2). The seal assembly 160 includes the hourglass-shaped seal 162 supported by upper and lower annular flanges 164, 166. The hourglass-shaped seal 162 of the seal assembly 160 is formed of an elastic material, e.g., rubber, and defines a central opening 163. The upper and lower flanges 164, 166 of the seal assembly 160 may be formed of the same of different material. In embodiments, the hourglass-shaped seal 162 may include one or more fabric layers. The hourglass-shaped seal 162 provides a seal around an outer surface of a surgical instrument passing through the valve assembly 120. The upper and lower annular flanges 164, 166 each define a plurality of openings 165, 167, respectively, corresponding to respective first and second sets of pins 188a extending from the respective upper and lower retainer members 182, 184 of the retainer assembly 180.

Referring back to FIGS. 2 and 4, the retainer assembly 180 of the valve assembly 120 is configured to secure the guard assembly 140 relative to the seal assembly 160, and secure the guard and seal assemblies 140, 160 to the centering mechanism 130. The retainer assembly 180 includes the upper retainer member 182, the lower retainer member 184, and a middle retainer member 186.

As noted above, the upper and lower retainer members 182, 184 include respective first and second pluralities of pins 188a, 188b. The first set of pins 188a extend from a bottom surface of the upper retainer member 182 and the second set of pins 188b extend from an upper surface of the lower retainer member 184. Each of the first and second sets of pins 188a, 188b are configured to be lockingly received within a plurality of openings 187 (FIG. 5) in the middle retainer member 186. In embodiments, the first and second sets of pins 188a, 188b are welded, glued, adhered, bonded or otherwise secured to each other and/or to the middle retainer member 186 within the plurality of openings 187 in the middle retainer member 186 to secure the upper, lower, and middle retainer members 182, 184, 186 together. Alternatively, the middle retainer member 186 may include locking features (not shown) for engaging the first and second sets of pins 188a, 188b.

With particular reference to FIG. 2, the first plurality of pins 188a of the upper retainer member 182 extend through the ring portion 142 of the guard assembly 140 and the upper flange 164 of the seal assembly 160. The second set of pins 188b of the lower retainer member 182 extend through the lower flange 166 of the seal assembly 160 and the inner annular ring 134 of the centering mechanism 130. The middle retainer member 186 is disposed between the upper and lower flanges 164, 166 of the seal assembly 160.

Although the retainer assembly 180 is shown with first and second pluralities of pins 188a, 188b, it is envisioned that the retainer assembly 180 may only include a first plurality of pins (not shown) having an increased length sufficient to engage openings (not shown) in the opposed retainer member.

During a surgical procedure utilizing cannula assembly 100, a surgical instrument (not shown) is introduced into the instrument valve housing 110 through the longitudinal passage 113 in the upper, lower, and inner housing sections 112, 114, 116. As described above, the distal end of the surgical instrument engages one or more of the first, second, third, and fourth petals 144, 146, 148, 150 of the guard assembly 140 causing the respective flap portions 144a, 146a, 18a, 150a to flex downward into contact with the hourglass-shaped seal 162 of the seal assembly 160 to cause the central opening 163 of the hourglass-shaped seal 162 to open to accommodate passage of the surgical instrument through the hourglass-shaped seal 162. The guard assembly 130 minimizes damage to the seal assembly 160 during insertion of an instrument through the valve assembly 120. The guard assembly 130 operates to protect the hourglass-shaped seal 162 of the seal assembly 160 from tearing or other damage as a surgical instrument is received through and withdrawn from the seal assembly 160.

With reference now to FIGS. 14-22, a valve assembly according to another embodiment of the present disclosure is shown generally as valve assembly 220. The valve assembly 220 is substantially similar to the valve assembly 120 (FIGS. 3 and 4) described hereinabove, and will only be described in detail as relates to the differences therebetween.

Figure 15:
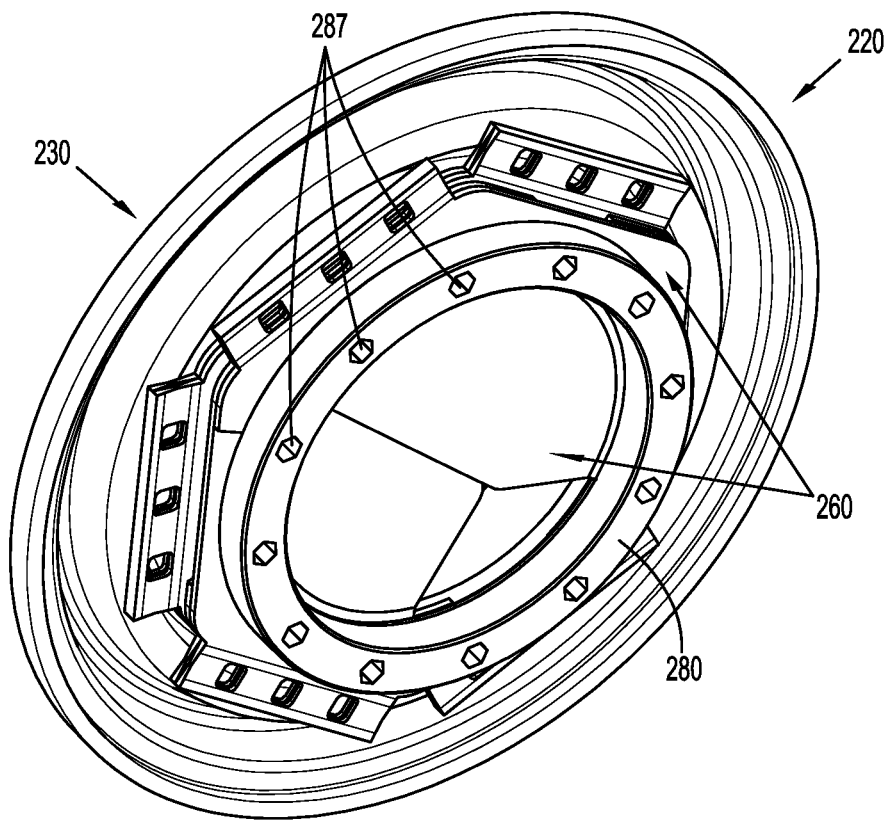
FIG. 15 is a perspective bottom view of the valve assembly shown in FIG. 14.
Figure 14:
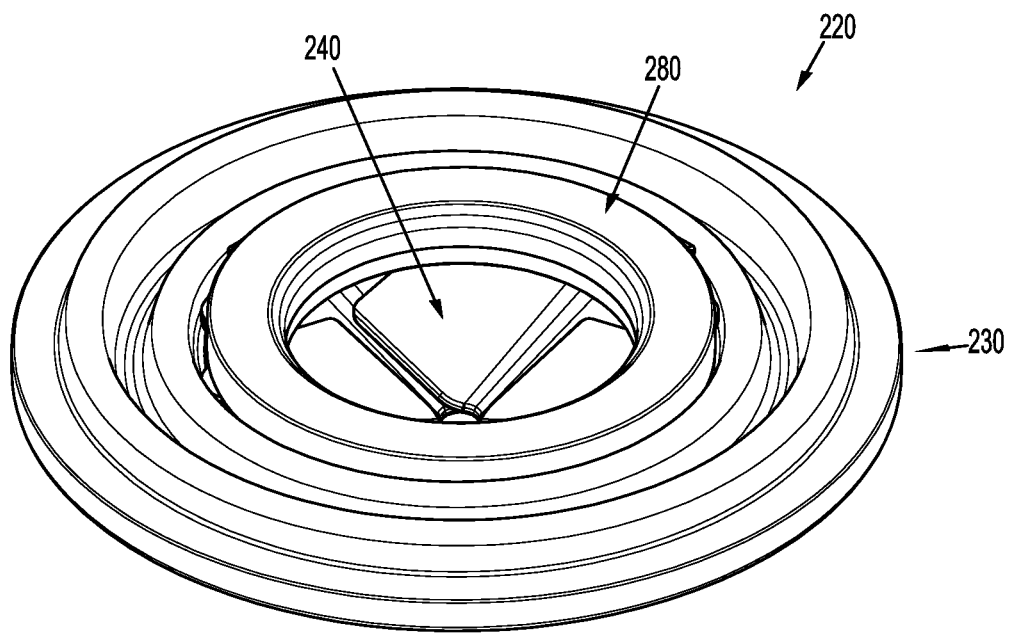
FIG. 14 is a perspective top view of a valve assembly according to another embodiment of the present disclosure.
Figure 16:
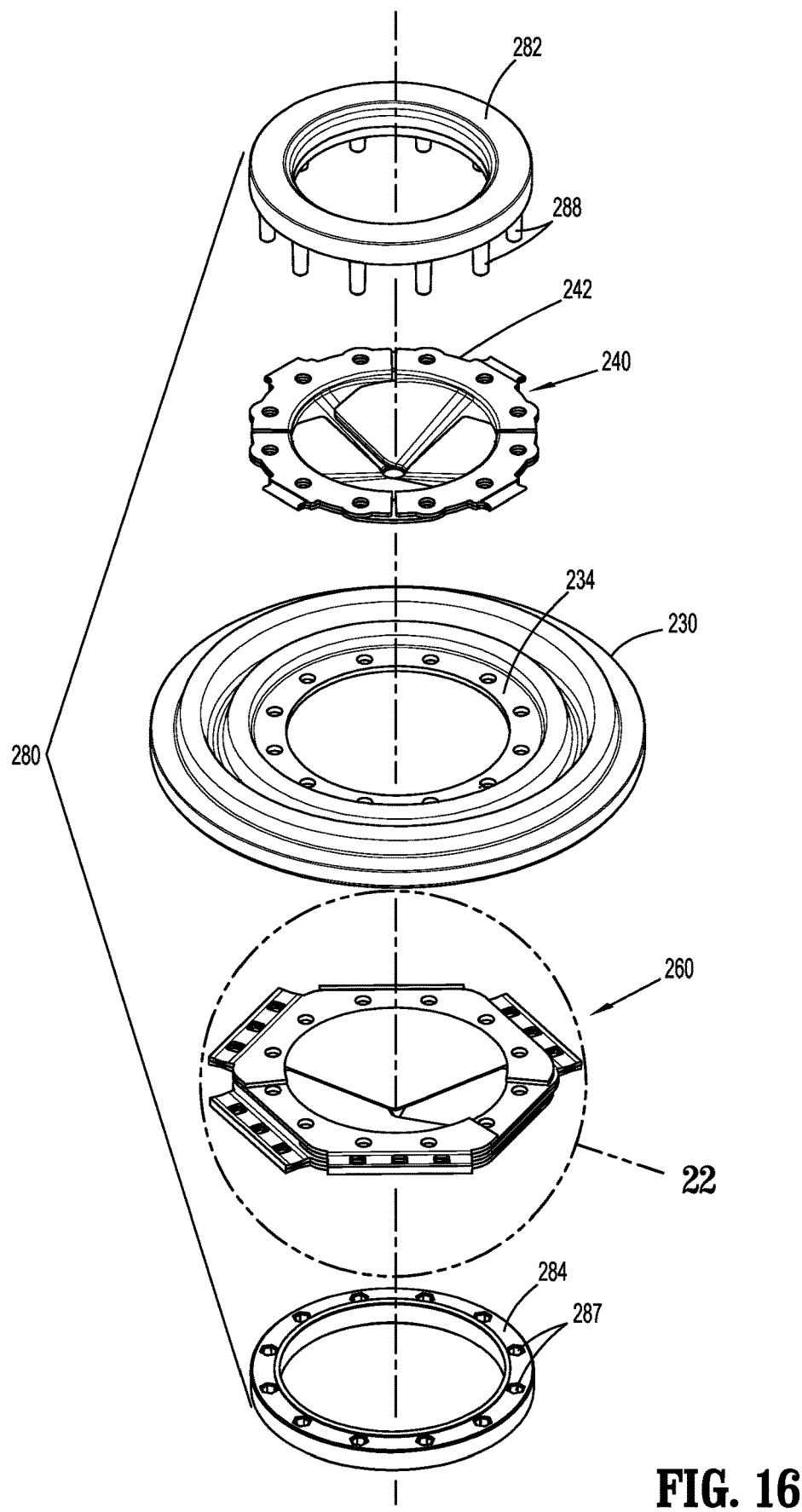
FIG. 16 is an exploded perspective view of the valve assembly shown in FIG. 14, including a centering mechanism, a guard assembly, a seal assembly, and a retainer assembly.
Figure 17:
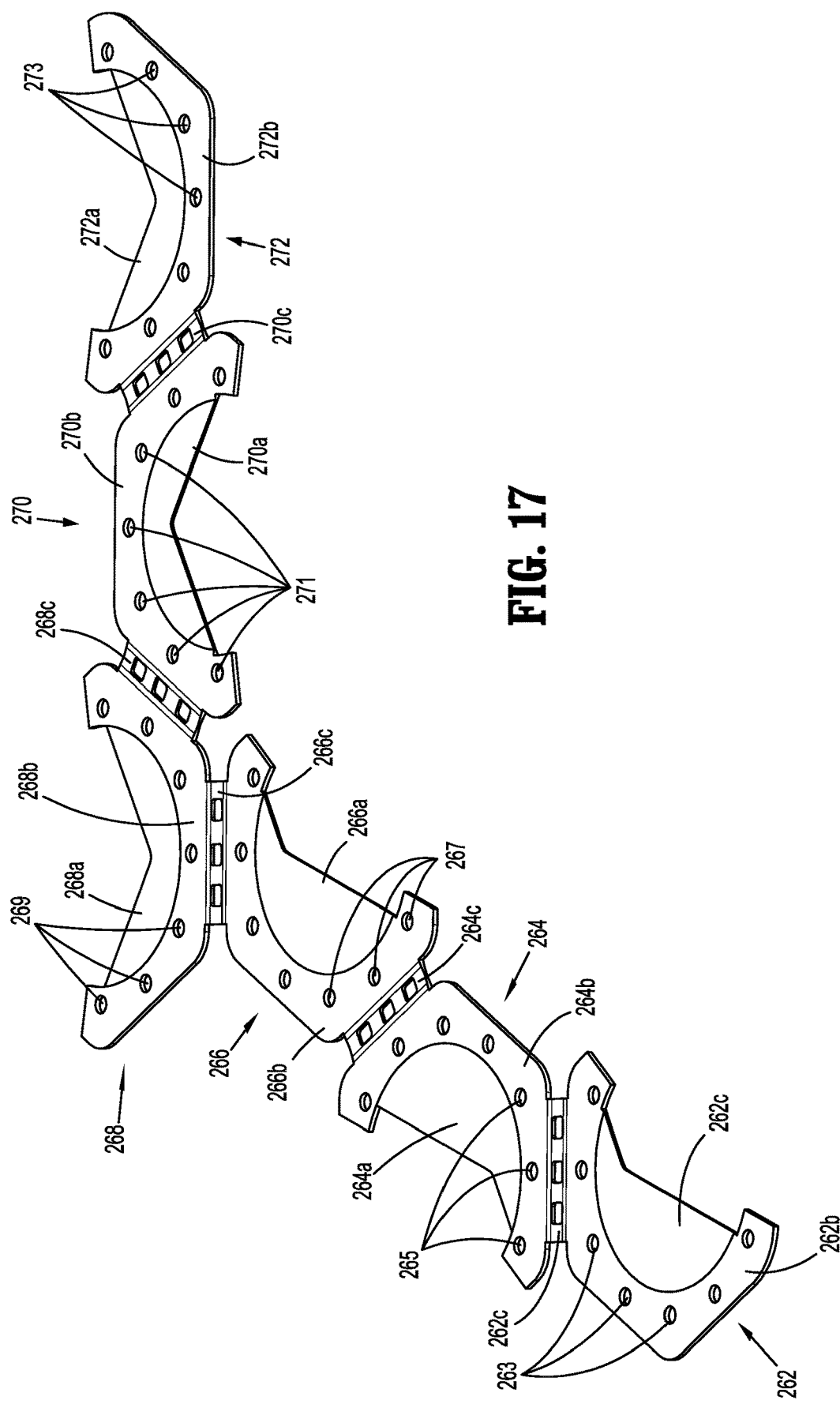
FIG. 17 is a perspective view of the seal assembly shown in FIG. 16, in an initial or unfolded condition.

Referring initially to FIGS. 14-16, the valve assembly 220 includes a centering mechanism 230, a guard assembly 240, a conical origami seal assembly 260, and a retainer assembly 280. The centering mechanism 230 and the guard assembly 240 are substantially similar to the centering mechanism 130 and the guard assembly 140 described above.

Referring to FIGS. 16-22, the seal assembly 260 of the valve assembly 220 is configured to provide a seal around an outer surface of a surgical instrument passing through the instrument valve housing 110 (FIG. 1). The seal assembly 260 includes first, second, third, fourth, fifth, and sixth petals or sections 262, 264, 266, 268, 270, 272 each having a seal portion 262a, 264a, 266a, 268a, 270a, 272a, respectively, and a respective base portion 262b, 264b, 266b, 268b, 270b, 272b supporting the respective seal portion 262a, 264a, 266a, 268a, 270a, 272a. The first and second sections 262, 264, the second and third sections 264, 266, the third and fourth sections 266, 268, the fourth and fifth sections 268, 270, and the fifth and sixth section 270, 272 are connected to one another by a connector portion 262c, 264c, 266c, 268c, 270c, respectively.

The seal portions 262a, 264a, 266a, 268a, 270a, 272a of the respective first, second, third, fourth, fifth, and sixth petals or sections 262, 264, 266, 268, 270, 272 of the seal assembly 260 are formed of an elastic material, e.g., rubber, and define a semi-conical shape. In embodiments, the seal assembly 260 is formed of polyisoprenes or silicone elastomers. The base portions 262b, 264b, 266b, 268b, 270b, 272b of the respective first, second, third, fourth, fifth, and sixth sections 262, 264, 266, 268, 270, 272 of the seal assembly 260 may be formed of the same or different materials as the respective seal portions 262a, 264a, 266a, 268a, 270a, 272a. In embodiments, the seal portions 262a, 264a, 266a, 268a, 270a, 272a may include one or more fabric layers.

The seal portions 262a, 264a, 266a, 268a, 270a, 272a of the first, second, third, fourth, fifth, and sixth petals or sections 262, 264, 266, 268, 270, 272, respectively, of the seal assembly 260 are configured to provide a seal around an outer surface of a surgical instrument (not shown) passing through the valve assembly 220. The seal portions 262a, 264a, 266a, 268a, 270a, 272a form a virtual inner circumferential surface for providing a seal bout the surgical instrument received through the instrument valve housing 110. The base portions 262b, 264b, 266b, 268b, 270b, 272b are substantially C-shaped members and each define a plurality of openings 263, 265, 267, 269, 271, 273, respectively, corresponding to a plurality of pins 288 (FIG. 16) extending from an upper retainer member 282 of the retainer assembly 280.

Figure 18:
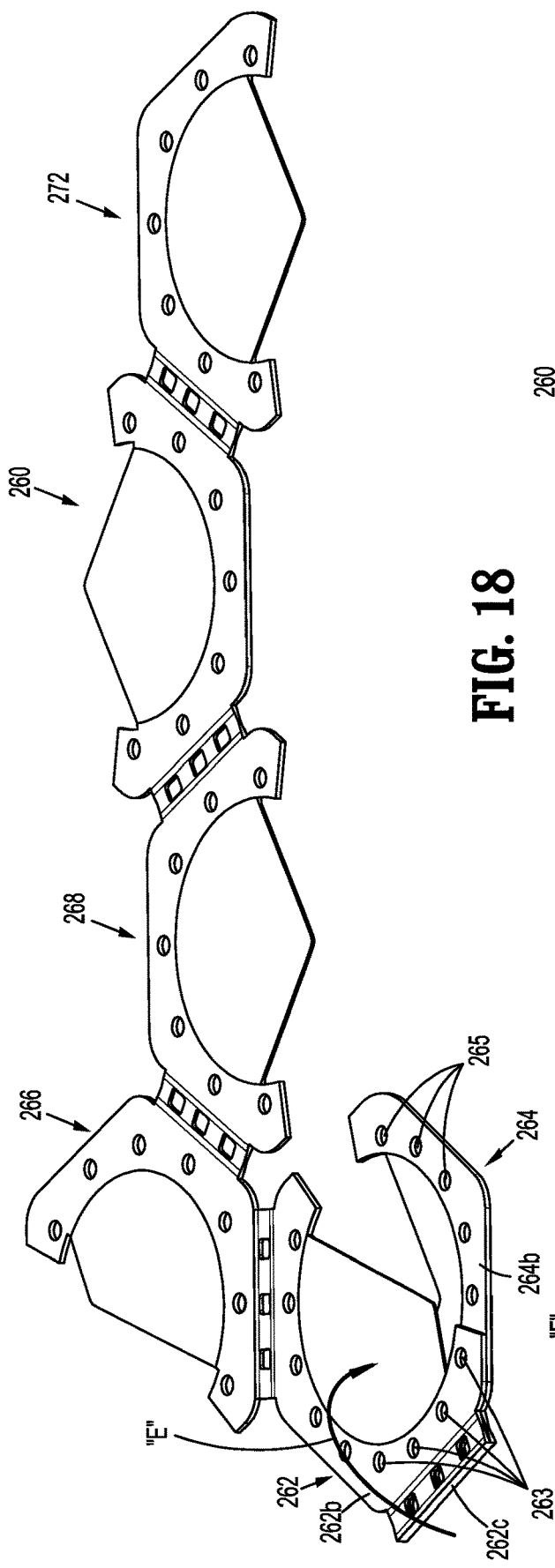
FIGS. 18-21 are perspective views of the guard assembly shown in FIG. 16, in sequential partially folded conditions.

The method of folding the conical origami seal assembly 260 will now be described with reference to FIGS. 18-22. Referring initially to FIG. 18, the first and second sections 262, 264 of the seal assembly 260 are folded at the hinge portions 262 between the first and second sections 262, 264 of the seal assembly 260, as indicated by arrow "E", such the length of the support portion 262b of the first section 262 adjacent the hinge portion 262c overlaps the length of the support portion 264b of the second section 264 of the seal assembly 260 adjacent the hinge portion 262c. In this manner, the plurality of openings 263 in the length of the support portion 262b of the first section 262 adjacent the hinge portion 262c aligns with the plurality of openings 265 in the overlapping length of the support portion 264b of the second section 264 of the seal assembly 260 adjacent the hinge portions 262c.

Figure 19:
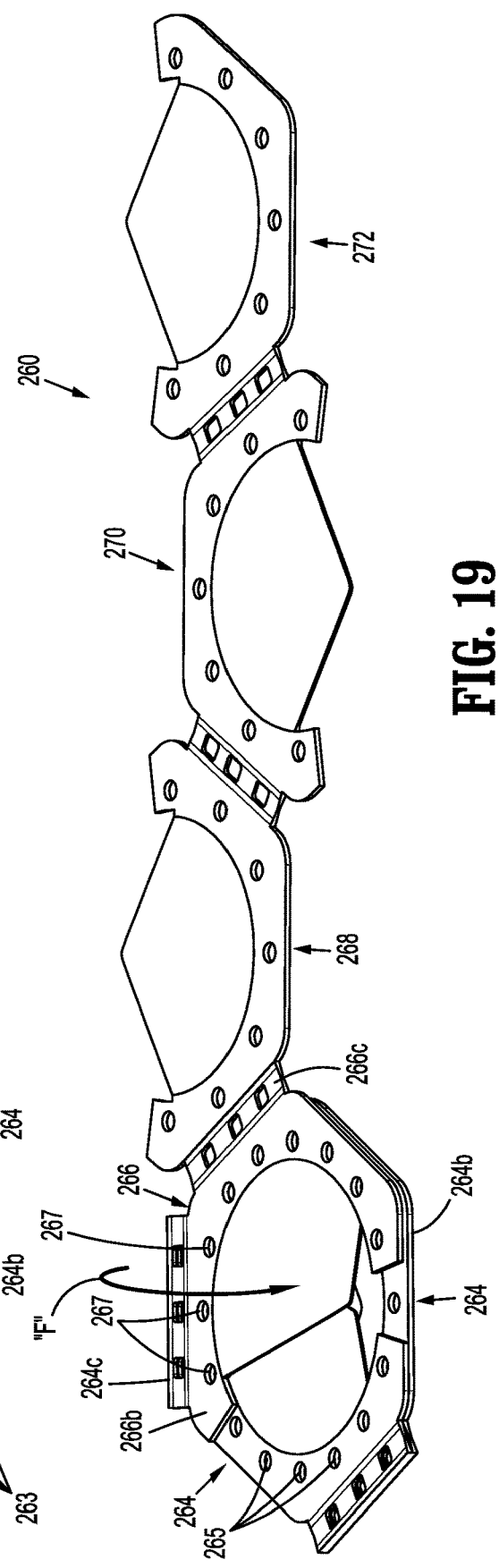

Turning to FIG. 19, the second and third sections 264, 266 of the seal assembly 260 are folded at the hinge portions 264c between the second and third sections 264, 266 of the seal assembly 260, as indicated by arrow "F", such the length of the support portion 264b of the second section 264 adjacent the hinge portion 264b overlaps the length of the support portion 266b of the third section 266 of the seal assembly 260 adjacent the hinge portion 264c. In this manner, the plurality of openings 265 in the length of the support portion 264b of the second section 264 adjacent the hinge portion 264c aligns with the plurality of openings 267 in the overlapping length of the support portion 266b of the third section 266 of the seal assembly 260 adjacent the hinge portions 264c.

Figure 20:
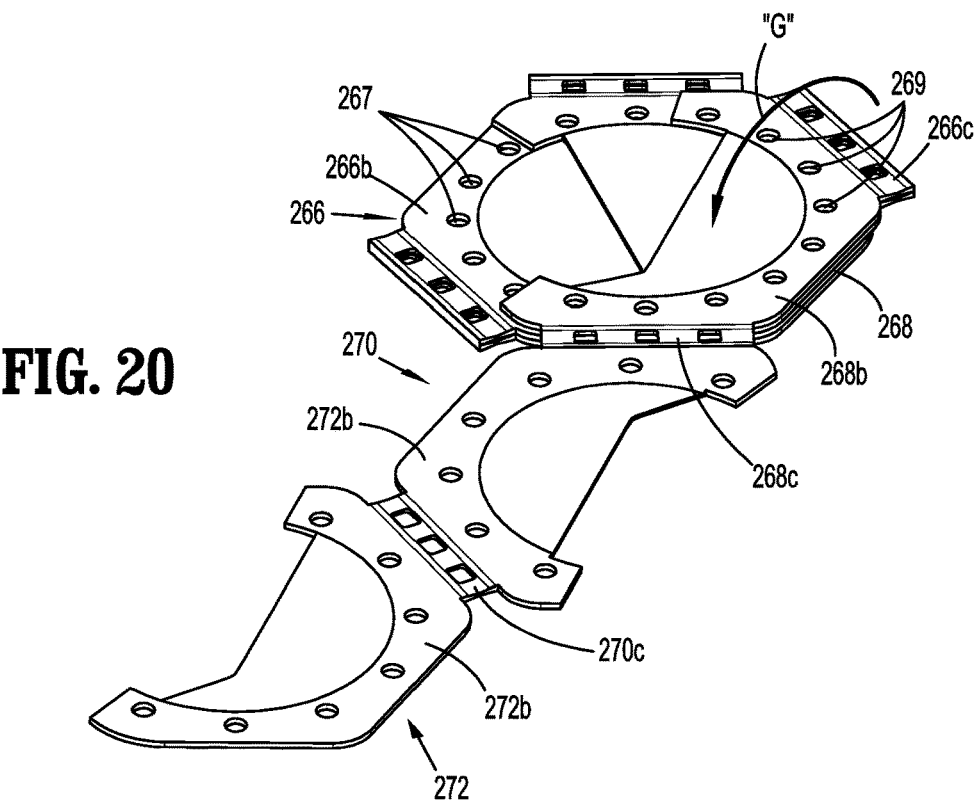

Referring to FIG. 20, the third and fourth sections 266, 268 of the seal assembly 260 are folded at the hinge portions 266c between the third and fourth sections 266, 268 of the seal assembly 260, as indicated by arrow "G", such the length of the support portion 266b of the third section 266 adjacent the hinge portion 266c overlaps the length of the support portion 268b of the fourth section 268 of the seal assembly 260 adjacent the hinge portion 266c. In this manner, the plurality of openings 267 in the length of the support portion 266b of the third section 266 adjacent the hinge portion 266c aligns with the plurality of openings 269 in the overlapping length of the support portion 268b of the fourth section 268 of the seal assembly 260 adjacent the hinge portions 266c.

Figure 21:
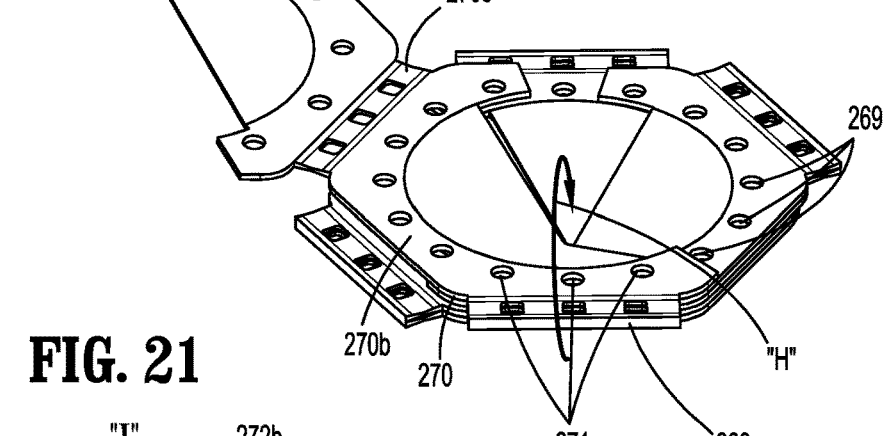

With reference to FIG. 21, the fourth and fifth sections 268, 270 of the seal assembly 260 are folded at the hinge portions 268c between the fourth and fifth sections 268, 270 of the seal assembly 260, as indicated by arrow "H", such the length of the support portion 268b of the fourth section 268 adjacent the hinge portion 268c overlaps the length of the support portion 270b of the fifth section 270 of the seal assembly 260 adjacent the hinge portion 268c. In this manner, the plurality of openings 269 in the length of the support portion 268b of the fourth section 268 adjacent the hinge portion 268c aligns with the plurality of openings 271 in the overlapping length of the support portion 270b of the fifth section 270 of the seal assembly 260 adjacent the hinge portions 268c.

Figure 22:
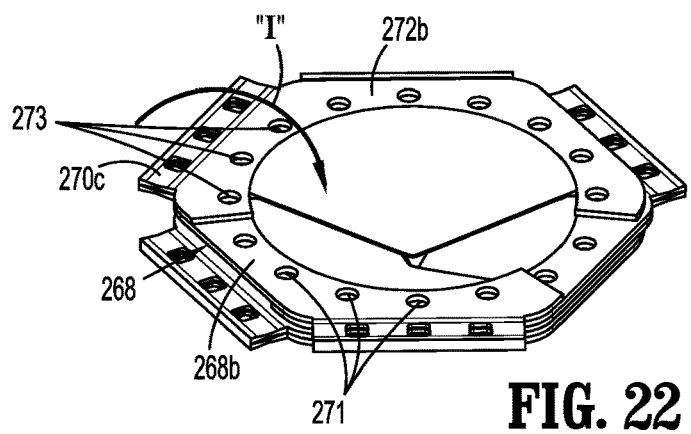
FIG. 22 is a perspective view of the guard assembly shown in FIG. 16, in a fully folded condition.

Turning to FIG. 22, the fifth and sixth sections 270, 272 of the seal assembly 260 are folded at the hinge portions 270c between the fifth and sixth sections 270, 272 of the seal assembly 260, as indicated by arrow "I", such the length of the support portion 270b of the fifth section 270 adjacent the hinge portion 270c overlaps the length of the support portion 272b of the sixth section 272 of the seal assembly 260 adjacent the hinge portion 270c. In this manner, the plurality of openings 271 in the length of the support portion 270b of the fifth section 270 adjacent the hinge portion 270c aligns with the plurality of openings 273 in the overlapping length of the support portion 272b of the sixth section 270 of the seal assembly 260 adjacent the hinge portions 270c.

Referring back to FIGS. 14-16, the retainer assembly 280 of the valve assembly 220 is configured to secure the guard assembly 240 relative to the seal assembly 260, and secure the guard and seal assemblies 240, 260 to the centering mechanism 230. The retainer assembly 280 includes the upper retainer member 282 and a lower retainer member 284. As noted above, the upper retainer member 282 includes a plurality of pins 288 (FIG. 15) extending from a bottom surface of the upper retainer 282. The bottom retainer 284 defines a plurality of openings 287 (FIG. 15) corresponding to the plurality of pins 288 in the upper retainer member 282. The plurality of pins 288 of the upper retainer member 282 are configured to be lockingly received within a plurality of openings 287 in the lower retainer member 282. In embodiments, the plurality of pins 288 of the upper retainer member 282 may be friction fit, welded, glued, adhered, bonded or otherwise secured within the plurality of openings 287 in the lower retainer member 284. Alternatively, the lower retainer member 284 may include locking features (not shown) for engaging the plurality of pins 288 of the upper retainer member 282.

The plurality of pins 288 of the upper retainer member 282 extend through a ring portion 242 of the guard assembly 240, through an inner annular ring 234 of the centering mechanism 230, and through the base portions 262b, 264b, 266b, 268b, 270b, 272b of the respective first, second, third, fourth, fifth, and sixth sections 262, 264, 266, 268, 270, 272 of the seal assembly 260.

Although the retainer assembly 280 is shown with the plurality of pins 288 extending from the upper retainer member 282, it is envisioned that the plurality of pins 288 may instead extend from the bottom retainer member 284, and/or the retainer assembly 280 may include a second plurality of pins (not shown) extending from the bottom retainer member 284.

In use, the valve assembly 220 operates in a substantially similar manner to the valve assembly 120 described herein above.

With reference now to FIGS. 23-35, a valve assembly according to another embodiment of the present disclosure is shown generally as valve assembly 320. The valve assembly 320 is substantially similar to the valve assembly 220 described hereinabove, and will only be described in detail as relates to the differences therebetween.

Figure 24:
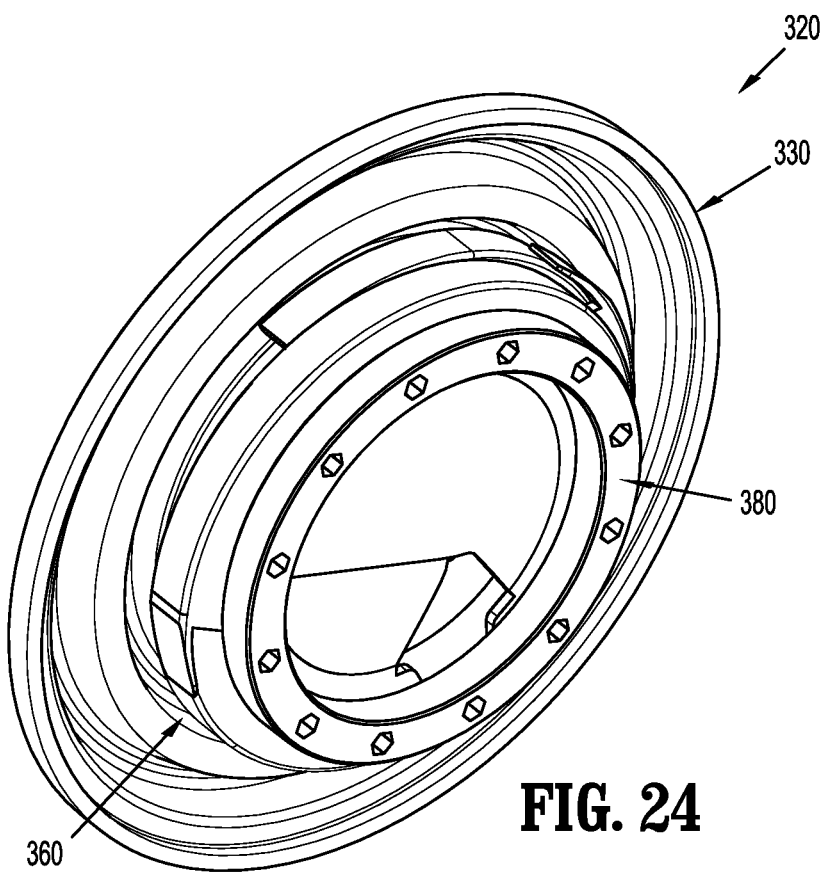
FIG. 24 is a perspective bottom view of the valve assembly shown in FIG. 23.
Figure 23:
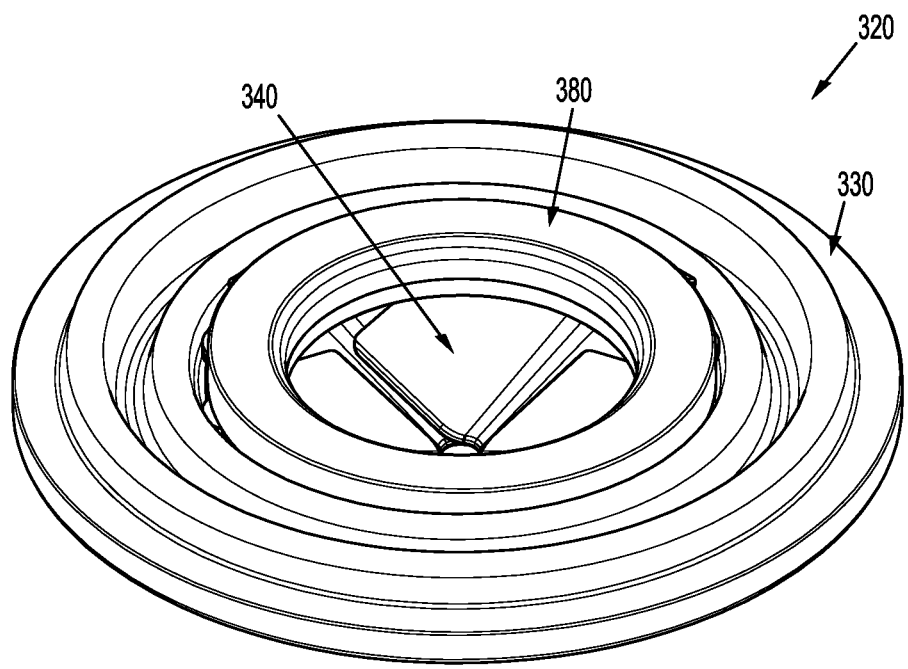
FIG. 23 is a perspective top view of a valve assembly according to another embodiment of the present disclosure.
Figure 25:
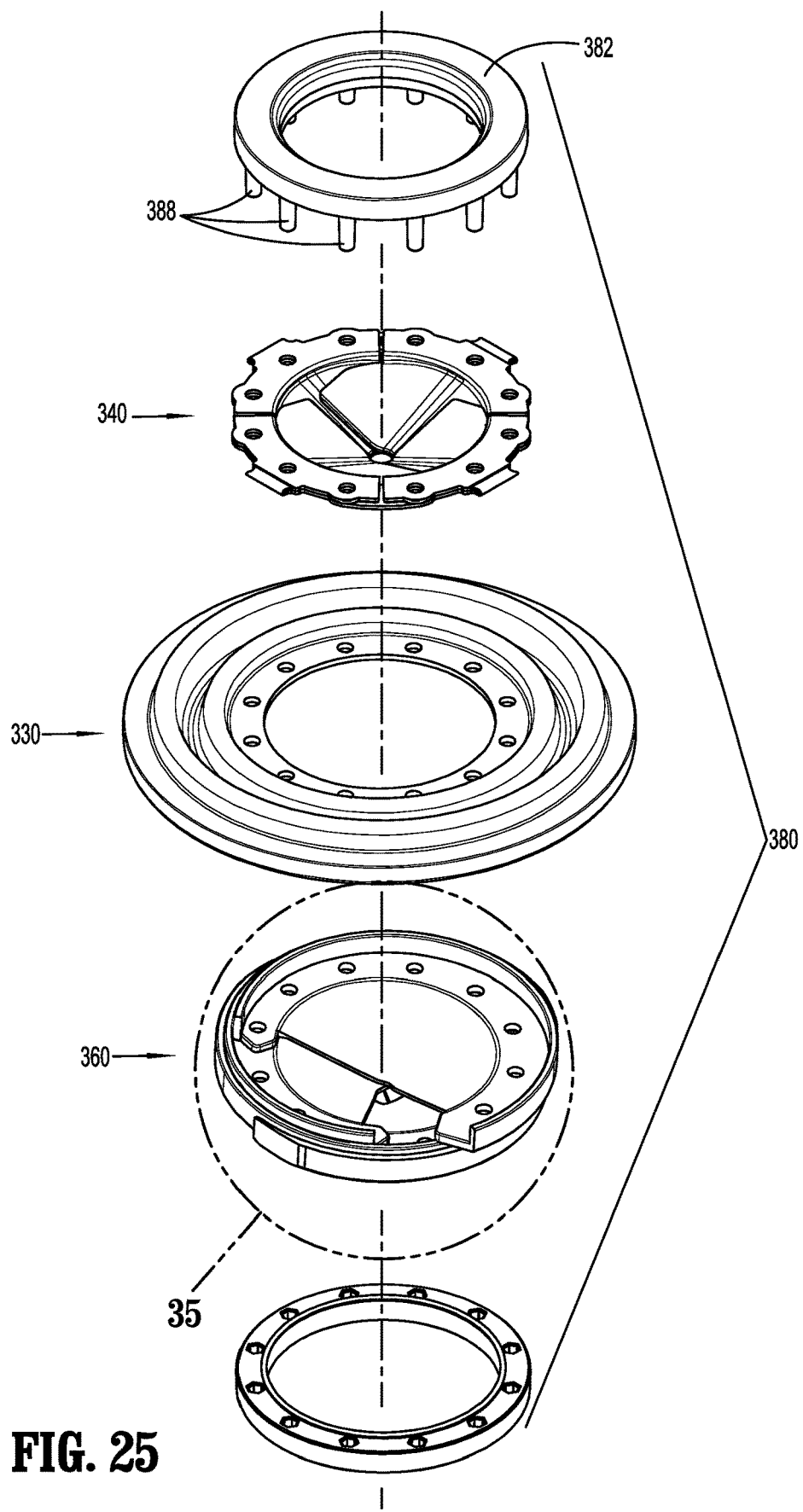
FIG. 25 is an exploded perspective view of the valve assembly shown in FIG. 23, including a centering mechanism, a guard assembly, a seal assembly, and a retainer assembly.

Referring initially to FIGS. 23-25, the valve assembly 320 includes a centering mechanism 330, a guard assembly 340, a seal assembly 360, and a retainer assembly 380. The centering mechanism 330, the guard assembly 340, and the retainer assembly 380 are substantially similar to the centering mechanisms 130, 230, and the guard assemblies 140, 240, and the retainer assembly 280 described above.

Referring to FIGS. 26-35, the seal assembly 360 of the valve assembly 320 is configured to provide a seal around an outer surface of a surgical instrument (not shown) passing through the instrument valve housing 110 (FIG. 1). The seal assembly 360 includes first, second, third, and fourth seal members 362, 364, 366, 368. The multiple seal members 362, 364, 366, 368 form a virtual inner circumferential surface for providing a seal bout the surgical instrument received through the instrument valve housing 110. Although shown as independent components, it is envisioned that the first, second, third, and fourth seal members 362, 364, 366, 368 may be formed as a single component. The first, second and third seal members 362, 364, 366 are substantially similar.

Each of the first, second, third, and fourth seal members 362, 364, 366, 368 of the seal assembly 360 includes a seal portion 362a, 364a, 366a, 368a, respectively, a base portion 362b, 364b, 366b, 368b, respectively, supporting the respective seal portions 362a, 364a, 366a, 368a, and a rim portion 362c, 364c, 366c, 368c, respectively, extending about an outer perimeter of the respective base portions 362b, 364b, 366b, 368b.

The seal portions 362a, 364a, 366a, 368a, of the respective first, second, third, and fourth members 362, 364, 366, 368 of the seal assembly 360 are formed of an elastic material, e.g., rubber. In embodiments, the seal assembly 360 is formed of polyisoprenes or silicone elastomers. The base portions 362b, 364b, 366b, 368b of the respective first, second, third, and fourth seal members 362, 364, 366, 368 of the seal assembly 360 may be formed of the same or different materials as the respective seal portions 362a, 364a, 366a, 368a. In embodiments, the seal portions 362a, 364a, 366a, 368a may include one or more fabric layers.

The seal portions 362a, 364a, 366a, 368a of the first, second, third, and fourth seal members 362, 364, 366, 368, respectively, of the seal assembly 360 are configured to provide a seal around an outer surface of a surgical instrument passing through the valve assembly 320. The first, second, third, and fourth members 362, 364, 366, 368 form a shape that defines a wedge-shaped cutout. The base portions 362b, 364b, 366b, 368b and the rim portions 362c, 364c, 366c, 368c are substantially C-shaped members. Each of the base portions 362b, 364b, 366b, 368b define a plurality of openings 363, 365, 367, 369, respectively, corresponding to a plurality of pins 388 (FIG. 25) extending from an upper retainer member 382 of the retainer assembly 380.

Figure 26:
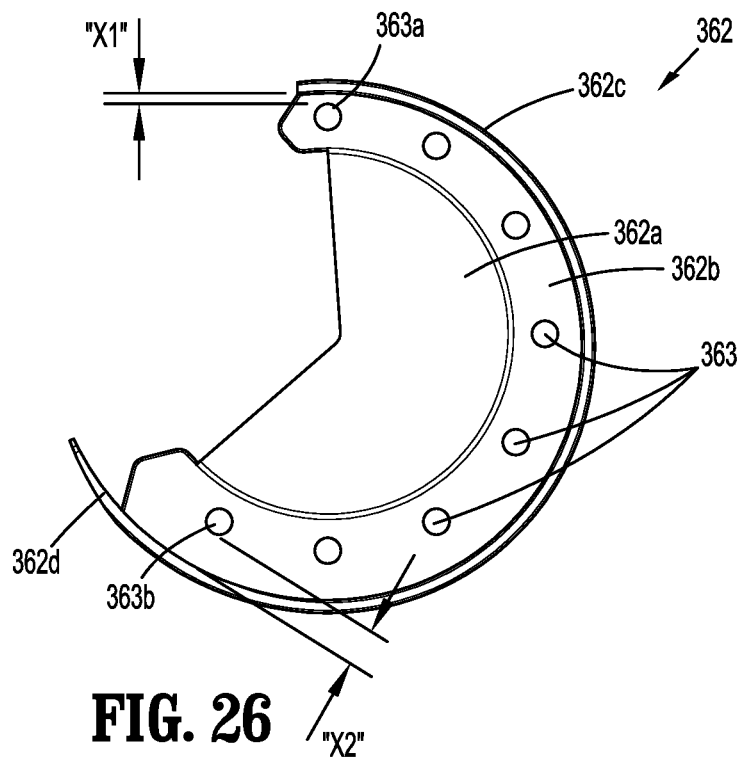
FIG. 26 is a top view of a first seal member of the seal assembly shown in FIG. 25.
Figure 27:
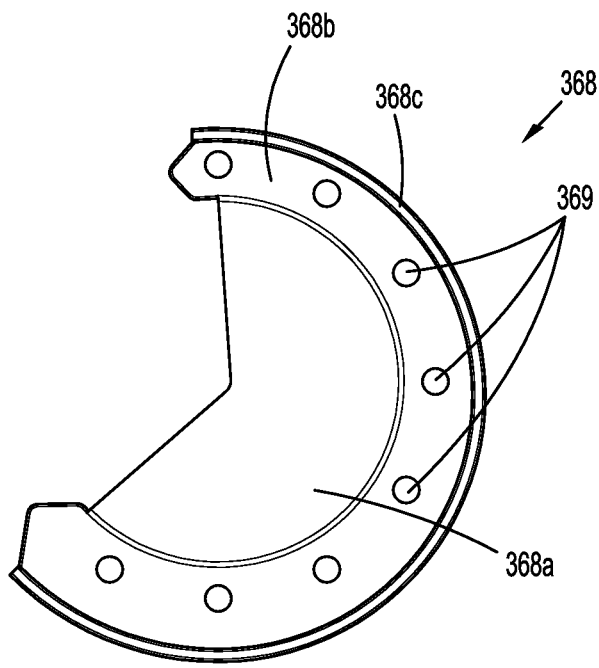
FIG. 27 is a perspective view of a fourth seal member of the seal assembly shown in FIG. 25.

A width of the base portions 362b, 364b, 366b, 368b of the first, second, third, and fourth seal members 362, 364, 366, 368 of the seal assembly 360 increases in a clockwise direction, as viewed in FIGS. 26 and 27. In this manner, using the first seal member 362 of FIG. 26 as an example, a distance "x1" between the rim portion 362c and a first opening 363a of the plurality of openings 363 of the base portion 362b is less than a distance "x2" between the rim portion 362c and a final opening 363b of the plurality of openings 363.

Each of the first, second, and third seal members 362, 364, 366 of the seal assembly 360 includes a tab 362d, 364d, 366d extending from the respective rim portions 362c, 364c, 366c. The tabs 362d, 364d, 366d facilitate assembly of the seal assembly 360.

Figure 28:
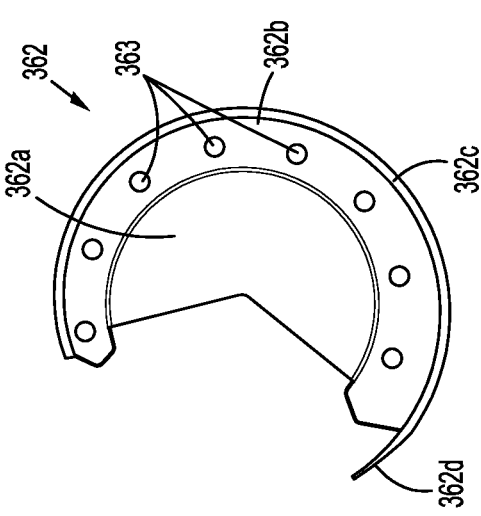

The method of assembling the seal assembly 360 will now be described with reference to FIGS. 28-35. Referring initially to FIG. 28, the first seal member 360 of the seal assembly 360 is positioned in a first orientation.

Figure 30:
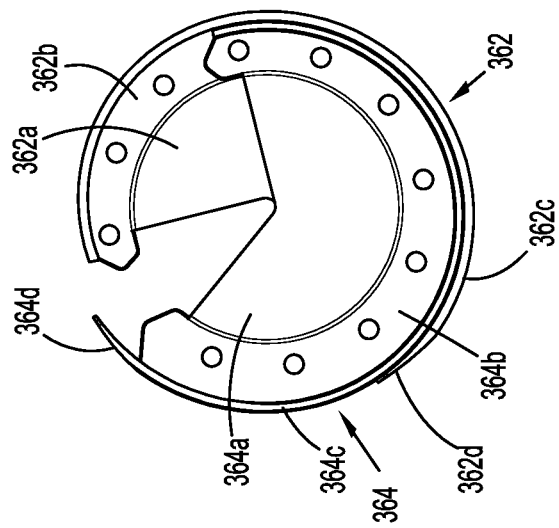
FIGS. 28-33 are a perspective side and top views of the method of assembling the seal assembly shown in FIG. 25.
Figure 29:
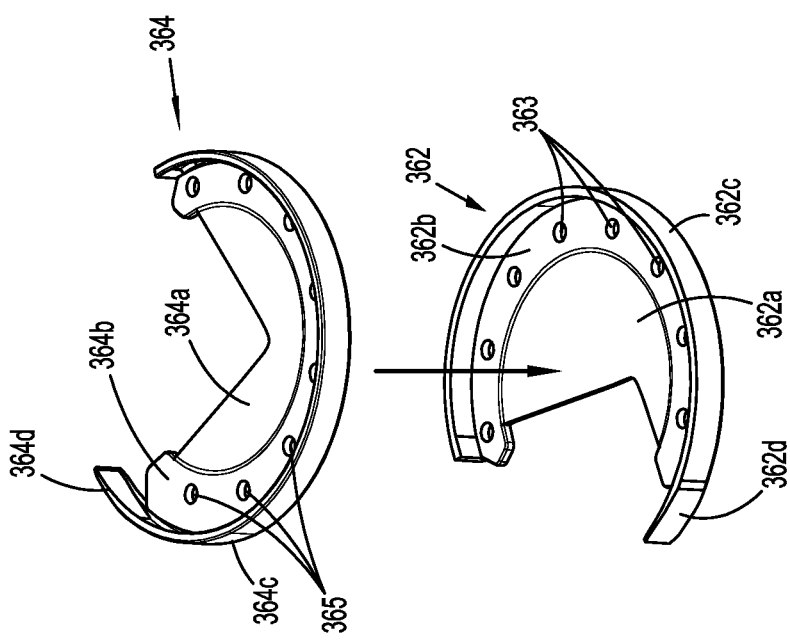

Turning to FIGS. 29 and 30, the second seal member 364 of the seal assembly 364 is received within the rim portion 362c of the first seal member 362. The second seal member 364 is rotationally offset from the first seal member 362. In embodiments, the first and second seal members 362, 364 are rotationally offset by ninety degrees (90°), although other offsets are envisioned.

Figure 32:
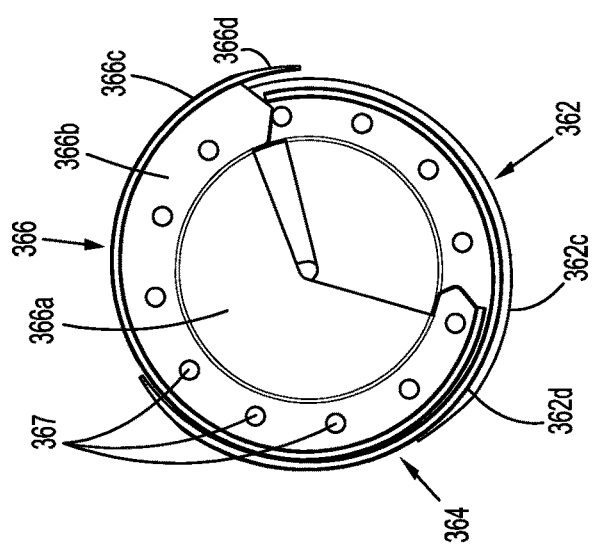
Figure 31:
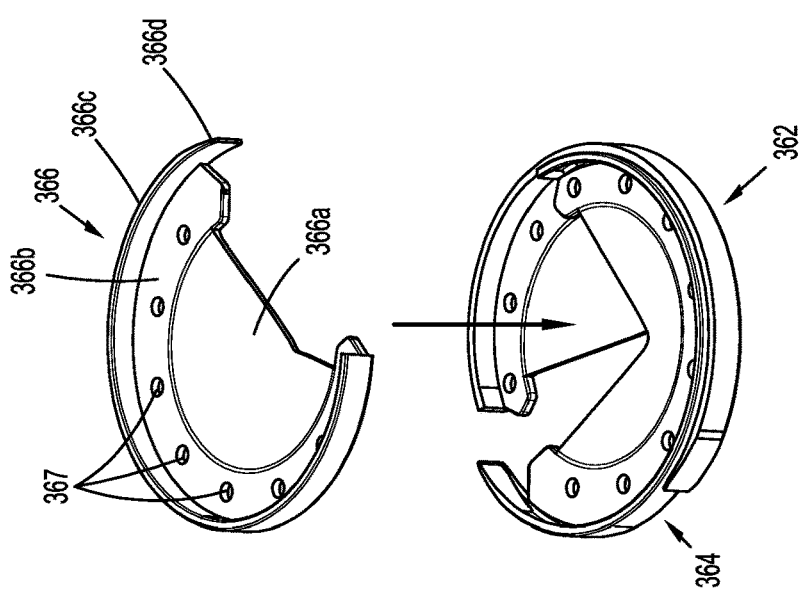

With reference to FIGS. 31 and 32, the third seal member 366 of the seal assembly 360 is then rotated relative to the second seal member 364 and received within the rim portion 364c of the second seal member 364 of the seal assembly 360.

Figure 33:
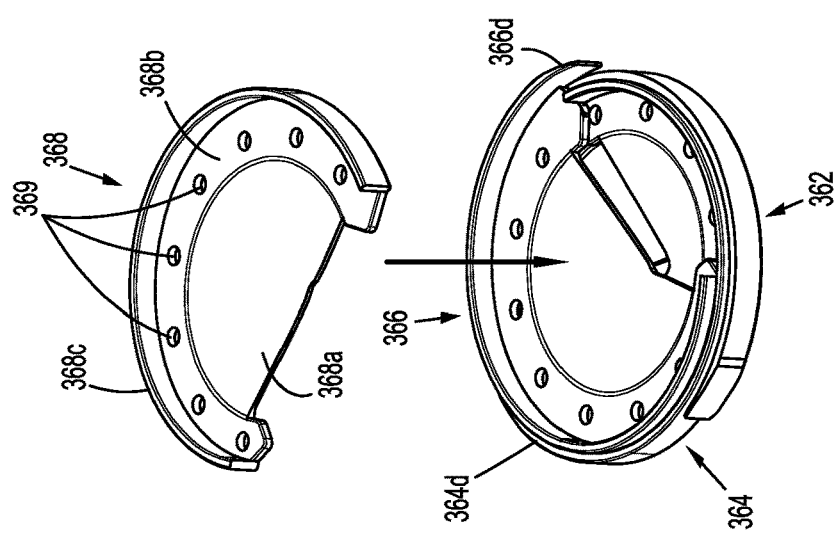
Figure 35:
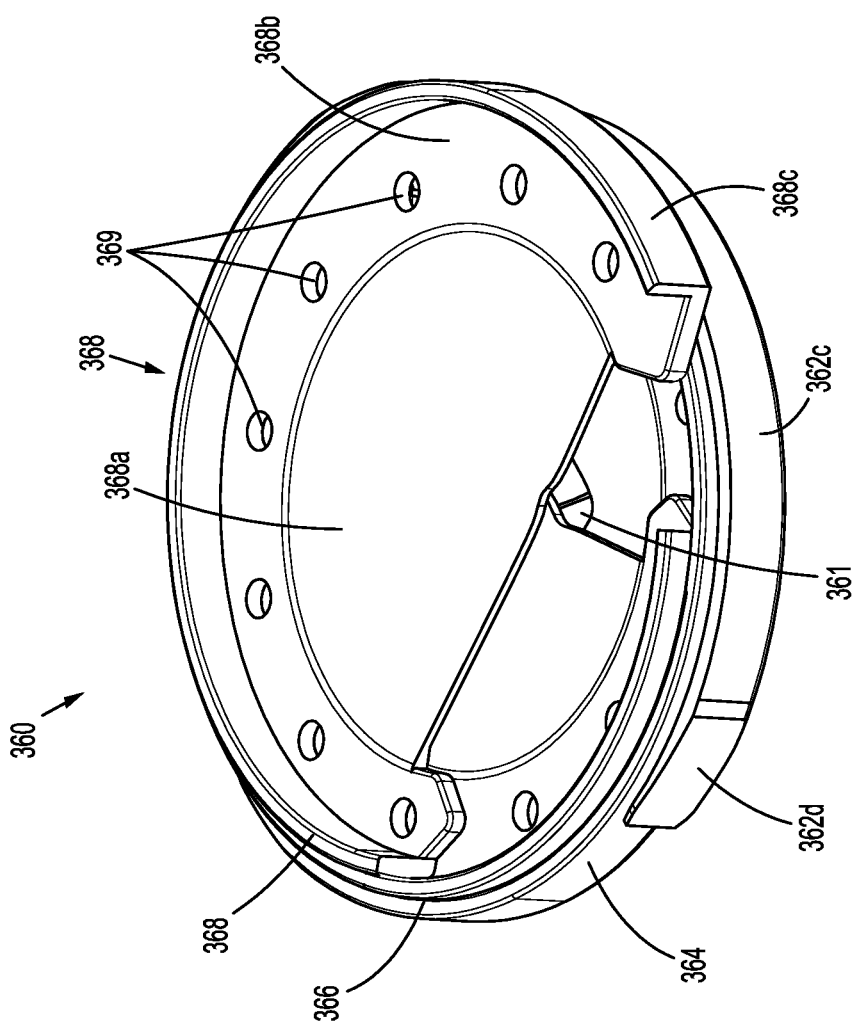
FIG. 35 is a perspective view of the seal assembly shown in FIG. 25.
Figure 34:
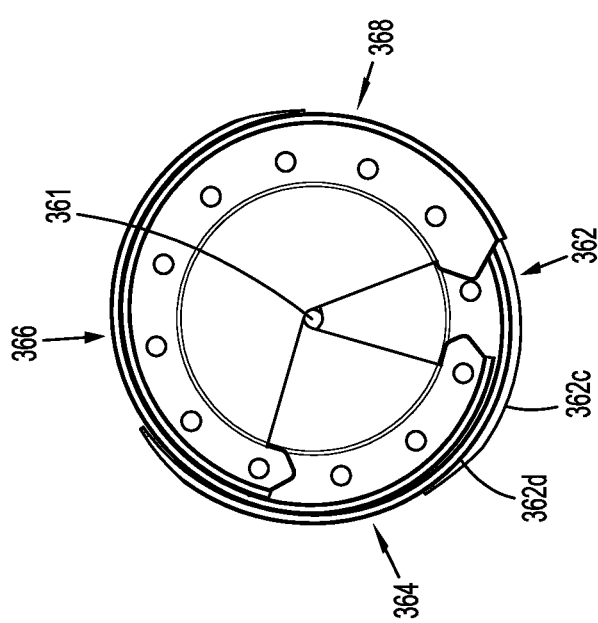
FIG. 34 is a top view of the seal assembly shown in FIG. 25.

Turning to FIGS. 33-35, the fourth seal member 368 of the seal assembly 360 is then rotated relative to the third seal member 366 and is received within the rim portion 366c of the third seal member 366 of the seal assembly 360.

Once assembled, the first, second, third, and fourth seal members 362, 364, 366, 368 are secured together by the plurality of pins 388 extending from the upper retainer member 382 (FIG. 25) of the retainer assembly 380.

The valve assembly 320 is receivable within an instrument valve housing, e.g., instrument valve housing 100 (FIG. 1), and operates in a similar manner to the seal assemblies 120, 220 described above.

With reference now to FIGS. 36-45, a seal assembly according to another embodiment of the present disclosure is shown generally as seal assembly 460. With initial reference to FIGS. 36-39, the seal assembly 460 includes first, second, third, fourth, fifth, and sixth seal segments or members 462, 464, 466, 468, 470, 472. The first, second, third, fourth, fifth, and sixth seal segments or members 462, 464, 466, 468, 470, 472 are stackable to form a seal having a virtual inner circumferential surface defining an opening 461 to facilitate sealed passage of a surgical instrument (not shown) through the seal assembly 460. In embodiments, the opening 461 is between about 0.025" and about 0.100" in diameter.

Figure 36:
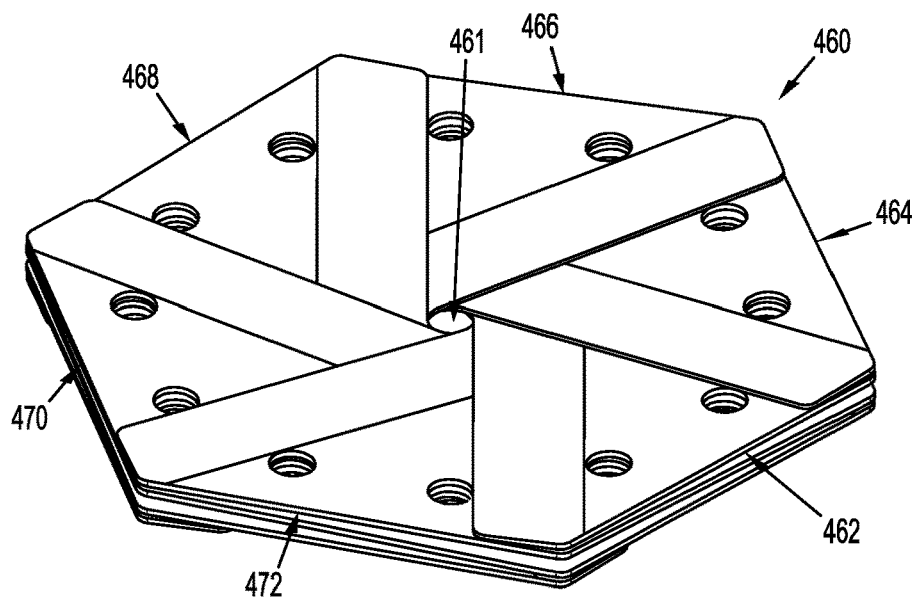
FIG. 36 is a perspective view of a seal assembly according to another embodiment of the present disclosure.
Figure 37:
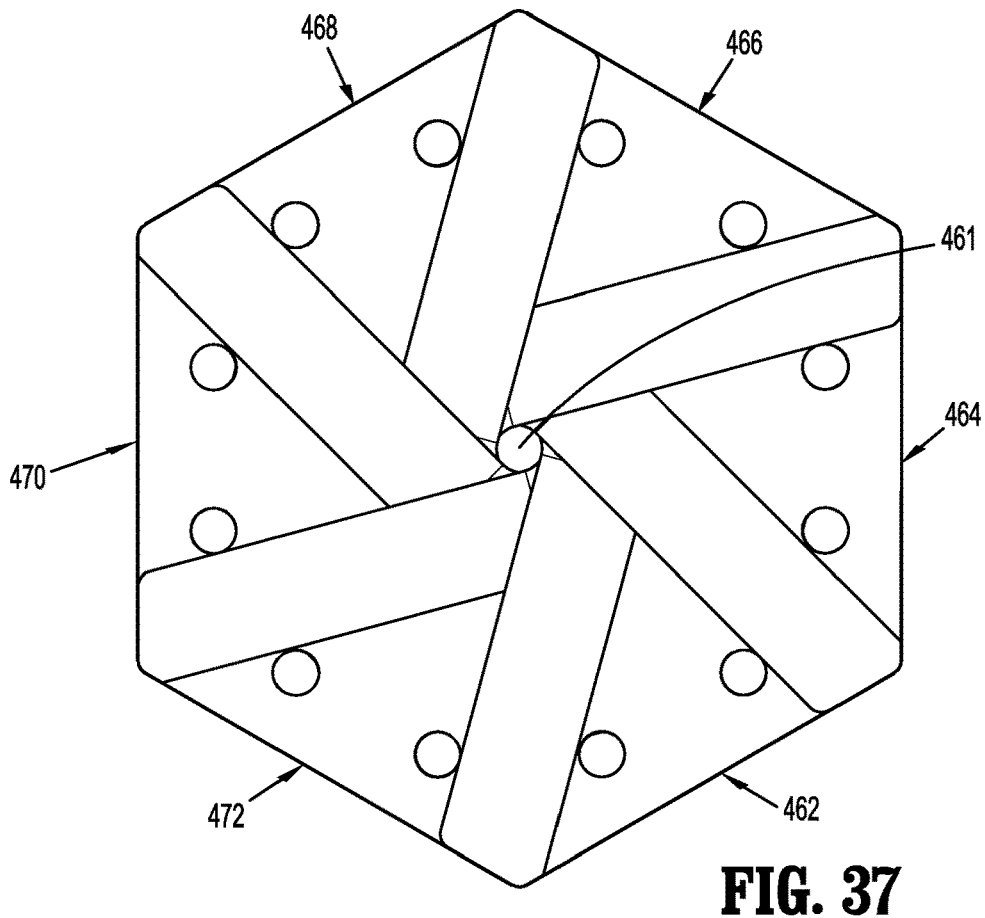
FIG. 37 is a top view of the seal assembly shown in FIG. 36.

With reference to FIGS. 36 and 37, the seal assembly 460 defines a substantially planar, hexagonal member. The hexagonal shape facilitates assembly of the seal assembly 460, allowing for quick placement of the seal segments in relation to each other, and/or by allowing for a quick vision check of the seal assembly 460 to ensure the seal segments 462, 464, 466, 468, 470, 472 are properly assembled. By forming the opening 461 out of multiple segments 462, 464, 466, 468, 470, 472, i.e., forming a virtual inner circumferential surface, instead of as a continuous solid opening through a single seal member, the likelihood of the seal assembly 460 tearing during insertion, removal, and/or use of a surgical instrument therethrough is greatly reduced. Although shown including six (6) segments, it is envisioned that the seal assembly 460 may include as few as four (4) segments, and as many as eight (8) segments.

The first, second, third, fourth, fifth, and sixth seal segments 462, 464, 466, 468, 470, 472 of the seal assembly 460 are formed of an elastic material, e.g., rubber, polyisoprene, or silicone elastomers. In one embodiment, the seal assembly 460 is formed of liquid silicon rubber (LSR). In embodiments, the first, second, third, fourth, fifth, and sixth segments 462, 464, 466, 468, 470, 472 may include one or more fabric layers.

Each of the first, second, third, fourth, fifth, and sixth seal segments 462, 464, 466, 468, 470, 472 of the seal assembly 460 are substantially similar, and therefore, will only be described in detail with respect to first seal segment 462.

Figure 38:
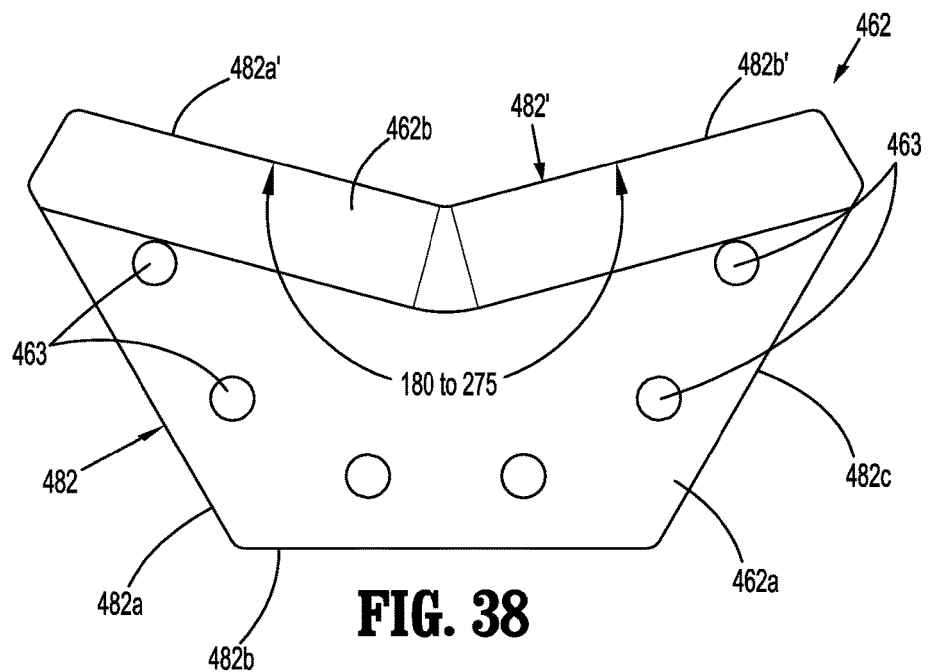
FIG. 38 is a top view of a seal section of the seal assembly shown in FIG. 36.
Figure 39:
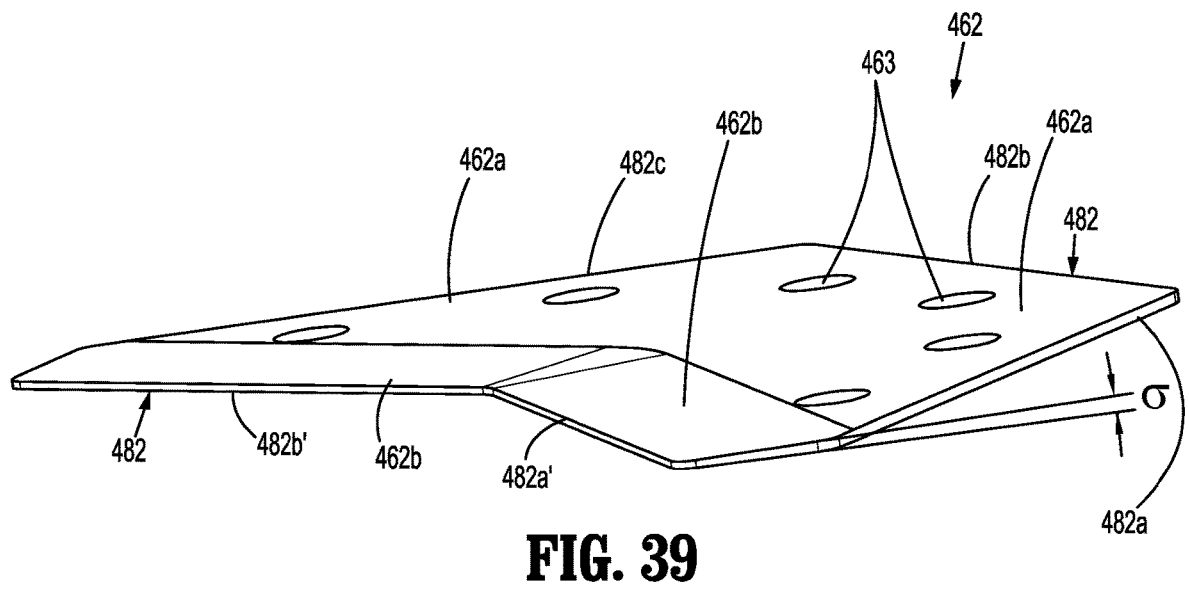
FIG. 39 is a perspective side view of the seal section shown in FIG. 38.

With particular to FIGS. 38 and 39, the first seal segment 462 of the seal assembly 460 is substantially wing-shaped and is configured to partially overlap the respective second, third, fourth, fifth, and sixth seal segments 464, 466, 468, 470, 472 when the seal assembly 460 is in the assembled or stacked configuration. The first seal segment 462 includes a base portion 462a and a seal portion 462b extending from the base portion 462a. The base portion 462a and the seal portion 462b may be formed of the same or different material.

The base portion 462a of the first seal segment 462 of the seal assembly 460 includes an outer edge 482. The outer edge 482 is formed of first, second, and third sections 482a, 482b, 482c. As will be described in further detail below, the first, second, and third sections 482a, 482b, 482c of the outer edge 482 facilitate assembly of the seal assembly 460. The base portion 462a of the first seal segment 462 defines a plurality of openings 463 to facilitate assembly and retention of the seal assembly 460 in the stacked configuration (FIG. 36). More particularly, the plurality of openings 463 are configured to receive pins, e.g., pins 188a (FIG. 5) of retaining assembly 180 of instrument valve assembly 120 (FIG. 3), for securing the seal segments 462, 464, 466, 468, 470, 472 relative to each other.

With particular reference to FIG. 39, the seal portion 462b of the first seal segment 462 of the seal assembly 460 may taper radially inwardly. As shown, the seal portion 426b of the first seal segment 462 is tapered at an angle "a" between leading and trailing portions of the seal portion 462b. In embodiments, the angle "a" is between about zero degrees (0°) and about fifteen degrees (15°). The tapered seal segment 462 may facilitate reception of a surgical instrument (not shown) through the seal assembly 460, and/or may enhance sealing about the surgical instrument.

With continued reference to FIGS. 38 and 39, the seal portion 462b of the first seal segment 462 of the seal assembly 460 includes an inner edge 482'. The inner edge 482' may extend straight across, or may include first and second sections 482a', 482b' that define a V-shape (as shown). In embodiments, the seal portion 462b defines an angle between about one-hundred eighty degrees (180°) and about two-hundred seventy-five degrees (275°). In one embodiment, and as shown, the seal portion 462b defines an angle of two-hundred ten degrees (210°).

Figure 41:
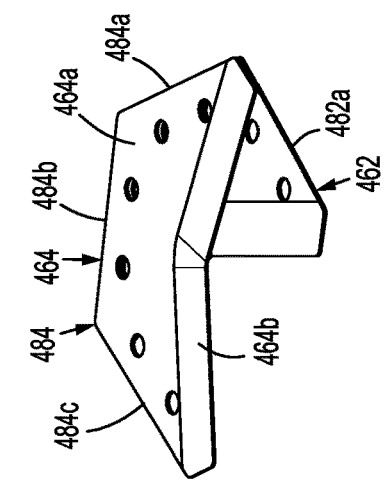
Figure 40:
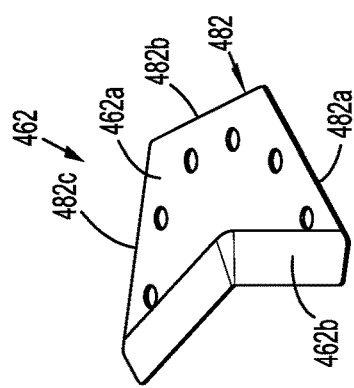

The method of assembly the seal assembly 460 will now be described with reference to FIGS. 40-45. Referring initially to FIG. 40, the first seal segment 462 of the seal assembly 460 is placed flat. Turning to FIG. 41, the second seal segment 464 is clocked sixty degrees (60°) in a counter-clockwise direction relative to the first seal segment 462, as shown, and is overlapped with the first seal segment 462 such that first and second outer edges 484a, 484b of the second seal segment 464 align with the second and third sections 482b, 482c (FIG. 40) of the first seal segment 462.

Figure 42:
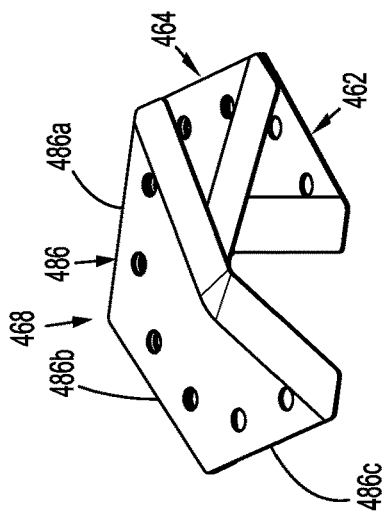
FIGS. 40-45 are perspective top views of a method of assembling the seal assembly shown in FIG. 36.

With reference to FIG. 42, the third seal segment 466 is clocked sixty degrees (60°) in a counter-clockwise direction relative to the second seal segment 464, as shown, and is overlapped with the second seal segment 464 such that first and second outer edges 486a, 486b of the third seal segment 466 align with the second and third sections 484b, 484c (FIG. 41) of the second seal segment 464.

Figure 43:
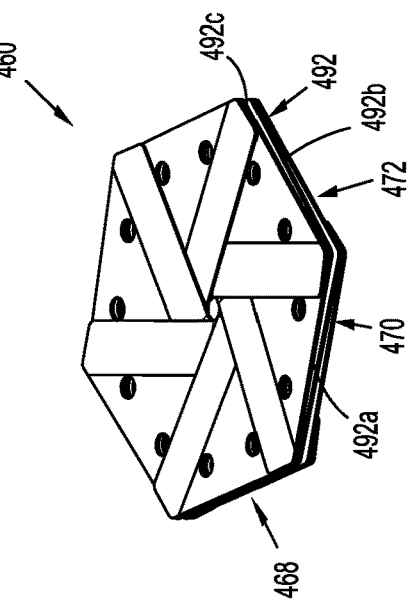

Now referring to FIG. 43, the fourth seal segment 468 is clocked sixty degrees (60°) in a counter-clockwise direction relative to the third seal segment 466, as shown, and is overlapped with the third seal segment 466 such that first and second outer edges 488a, 488b of the fourth seal segment 468 align with the second and third sections 486b, 486c (FIG. 42) of the third seal segment 466.

Figure 44:
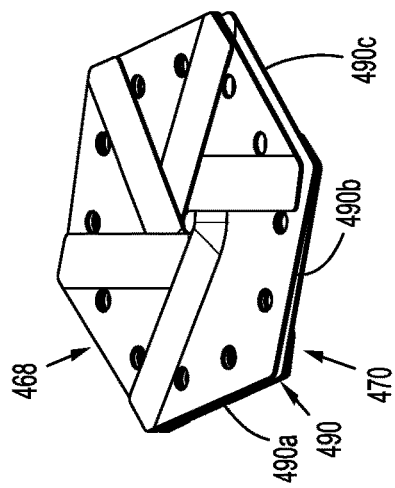

Turning to FIG. 44, the fifth seal segment 470 is clocked sixty degrees (60°) in a counter-clockwise direction relative to the fourth seal segment 468, as shown, and is overlapped with the fourth seal segment 468 such that first and second outer edges 490a, 490b of the fifth seal segment 470 align with the second and third sections 488b, 488c (FIG. 43) of the fourth seal segment 468.

Figure 45:
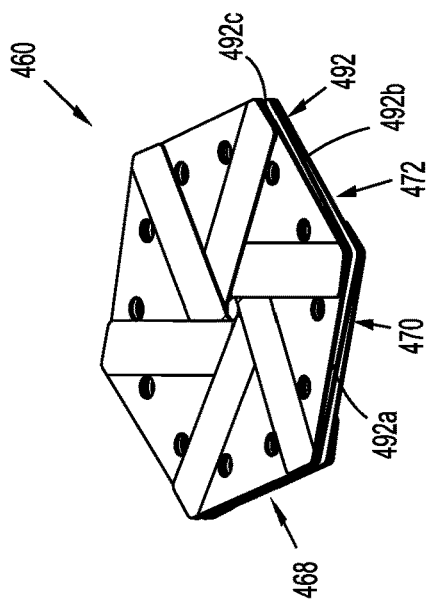

Turning to FIG. 45, the sixth seal segment 472 is clocked sixty degrees (60°) in a counter-clockwise direction relative to the fifth seal segment 470, as shown, and is overlapped with the fifth seal segment 470 such that first and second outer edges 492a, 492b of the sixth seal segment 472 align with the second and third sections 490b, 490c (FIG. 44) of the fifth seal segment 470. In embodiments, and as shown, a portion of the sixth seal segment 472 of the seal assembly 460 may be inserted under a portion of the first seal segment 462 to increase the integrity of the seal assembly 460.

In the assembled, or stacked configuration, the seal assembly 460 includes a substantially planar body having a substantially uniform thickness. It is envisioned that the aspects of the present disclosure may be modified for use with an access assembly having a substantially conical body.

Misalignment of any one of the seal segments of the seal assembly 460 may compromise the integrity of the seal assembly 460. As noted above, the configuration of the seal assembly 460 permits visual inspection of the seal assembly 460 to determine if the seal assembly 460 is assembled properly.

The seal assembly 460 may be modified for use in any of the above-described instrument valve assemblies.

Centering mechanisms according to alternative embodiments of the present disclosure will now be described with reference to FIGS. 46-50. The centering mechanisms will only be described to the extent necessary to fully disclose the aspects of the present disclosure, for a detailed description of the structure and function of an exemplary centering mechanism, please refer to commonly owned U.S. Pat. App. Pub. No. 2015/0025477 ("the '477 publication"), the content of which is incorporated herein by reference in its entirety. It is envisioned that the centering mechanisms may include two centering mechanisms, as disclosed in the '477 publication.

Figure 46:
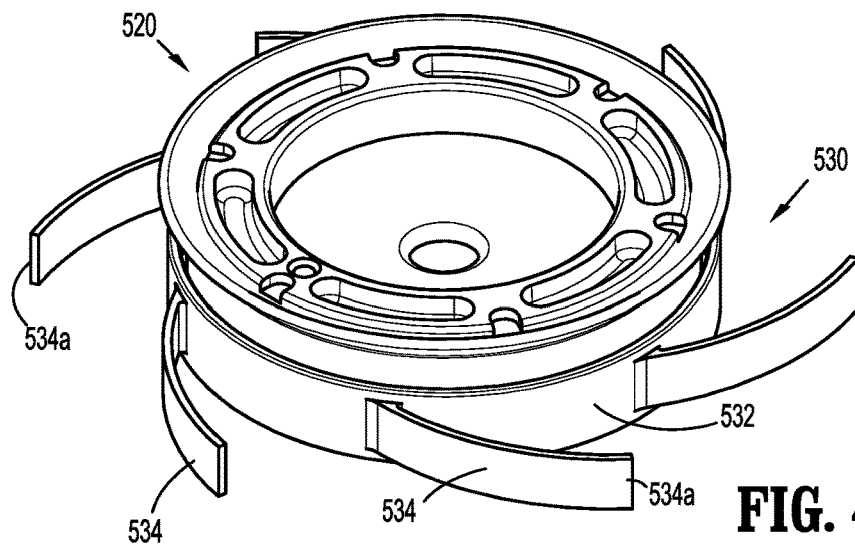
FIG. 46 is a top perspective view of a centering mechanism according to an embodiment of the present disclosure, including a seal assembly.
Figure 47:
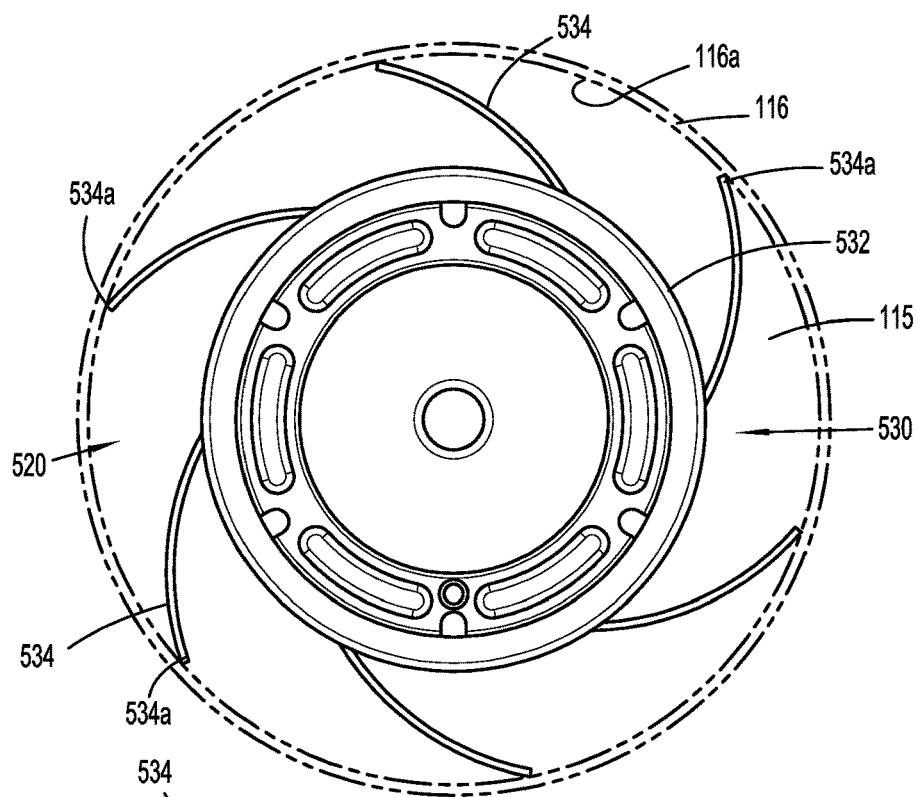
FIG. 47 is a top view of the centering mechanism and seal assembly shown in FIG. 46, disposed within an instrument valve housing.

Referring initially to FIGS. 46 and 47, a centering mechanism according to an embodiment of the present disclosure is shown generally as centering mechanism 530. The centering mechanism 530 is a component of a valve assembly 520 and is configured to permit radial movement of the valve assembly 520 relative to the instrument valve housing 110 (FIG. 1) when a surgical instrument (not shown) is received through the valve assembly 520, and returns the valve assembly 520 to a centered position once the surgical instrument is withdrawn from within the instrument valve housing 110.

The centering mechanism 530 includes an annular ring 532 and a plurality of spokes or spring elements 534 extending radially outward from the annular ring 532. Each spoke 534 of the plurality of spokes 534 of the centering mechanism 530 includes a free end 534a. The free ends 534a of the plurality of spokes 534 are configured to engage an inner wall 116a (FIG. 47) of the inner housing section 116 of the instrument valve housing 110 (FIG. 1) when received within a cavity 115 defined by the inner housing section 116. In this manner, the centering mechanism 530 is spring loaded when received within the instrument valve housing 110, thereby providing improved spring back for the valve assembly 520 when the valve assembly 520 is moved off-center.

Figure 48:
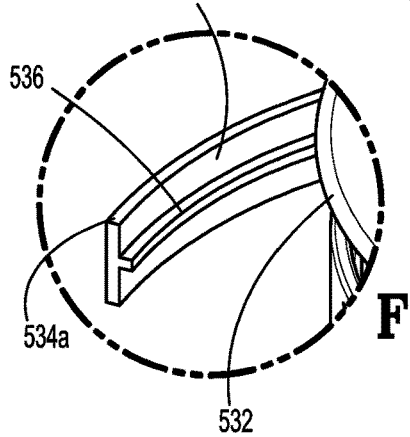
FIG. 48 is an enlarged view of a spoke of a centering mechanism according to another embodiment of the present disclosure.

With particular reference to FIG. 48, in embodiments, the plurality of spokes 534 may include one or more longitudinal ribs 536 extending along a length of the spokes 534. The ribs 536 reinforce the plurality of spokes 534 and provide an increased spring back.

Figure 49:
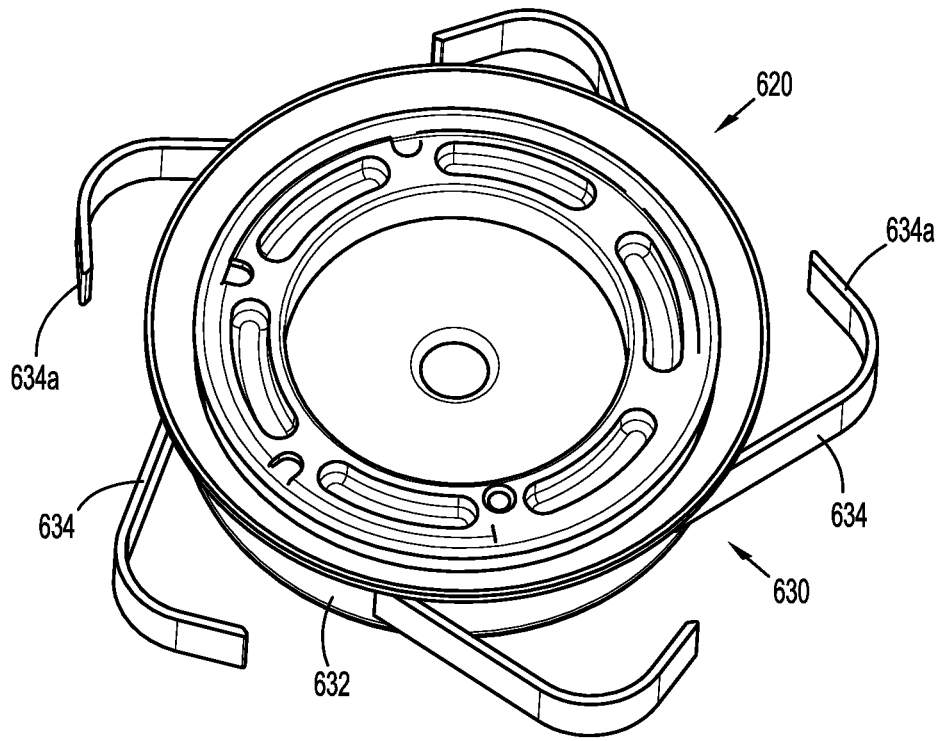
FIG. 49 is a top perspective view of a centering mechanism according to another embodiment of the present disclosure, including a seal assembly.
Figure 50:
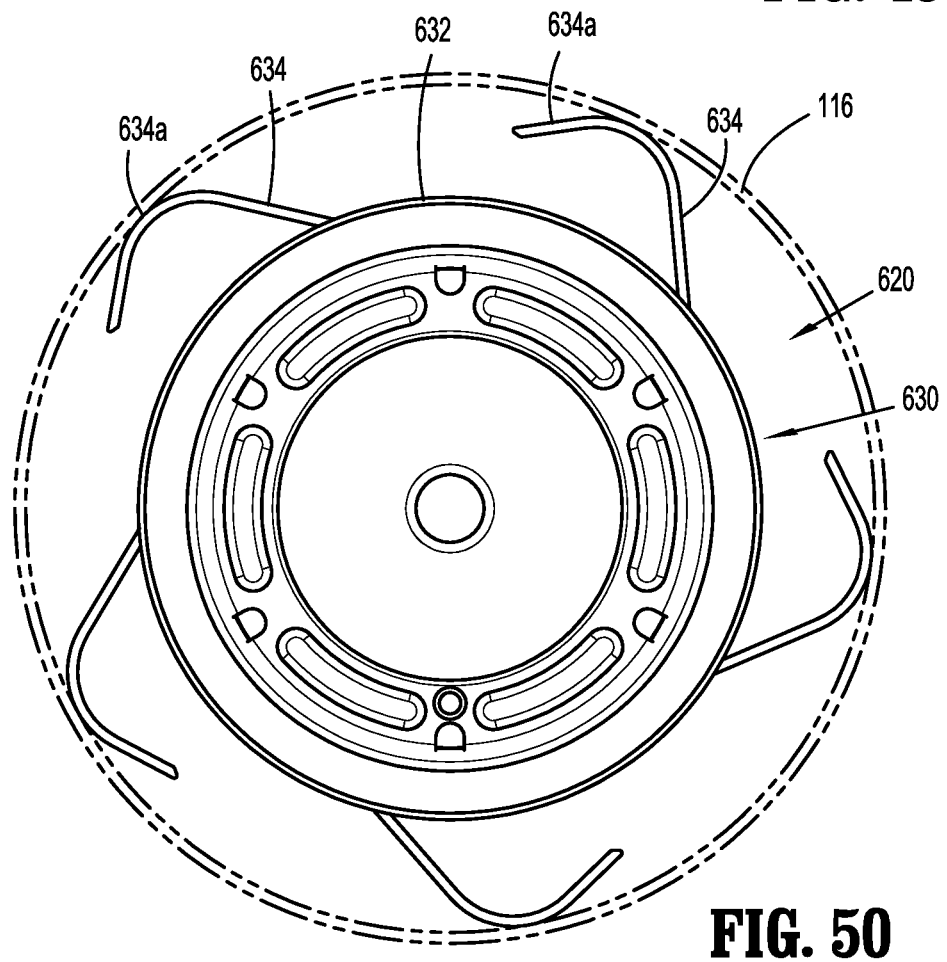
FIG. 50 is a top view of the centering mechanism and seal assembly shown in FIG. 49, disposed within an instrument valve housing.

Turning to FIGS. 49 and 50, another centering mechanism according to an embodiment of the present disclosure is shown generally as centering mechanism 630. The centering mechanism 630 is substantially similar to centering mechanism 530 described herein above, and therefore, will only be described as relates to the differences therebetween.

The centering mechanism 630 includes an annular ring 632 and a plurality of spokes or spring elements 634 extending radially outward from the annular ring 632. Each spoke 634 of the plurality of spokes 634 of the centering mechanism 630 includes a free end 634a. The free ends 634a of the plurality of spokes 634 are bent to provide increased spring back to the valve assembly 620.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. An access assembly comprising:
    an instrument valve housing including an upper housing section, a lower housing section, and an inner housing section, the instrument valve housing defining a cavity; and
    a valve assembly disposed within the cavity of the instrument valve housing, the valve assembly including:
        a guard assembly,
        a seal assembly disposed adjacent the guard assembly, the seal assembly including a plurality of seal segments, each seal segment of the plurality of seal segments attached to at least one other seal segment of the plurality of seal segments by a connector, the plurality of seal segments transitionable from an unfolded configuration to a folded configuration, the folded configuration defining a substantially hexagonal body, each seal segment of the plurality of seal segments includes a base portion and a seal portion extending from the base portion, each of the base portions including an outer edge formed of three segments, wherein each seal segment of the plurality of seal segments is disposed relative to an adjacent seal segment of the plurality of seal segments such that two of the three segments of the outer edge of the respective seal segments align with each other; and
        a centering mechanism for biasing the seal assembly and the guard assembly towards a center of the cavity of the instrument valve housing.

2. The access assembly of claim 1, wherein each seal segment of the plurality of seal segments is rotated sixty degrees (60°) relative to an adjacent seal segment of the plurality of seal segments.

3. The access assembly of claim 1, wherein the seal portions of the plurality of seal segments taper radially inward.

4. The access assembly of claim 1, wherein the seal portions of the plurality of seal segments defines an opening.

5. The access assembly of claim 4, wherein the opening includes a diameter from about 0.025" to about 0.100".

6. The access assembly of claim 1, wherein the seal portions of the plurality of seal segments form an angle from about 180° to about 275°.

7. The access assembly of claim 6, wherein the angle is 2100.

8. The access assembly of claim 1, wherein the plurality of seal segments includes six (6) seal segments.

9. The access assembly of claim 1, wherein the plurality of seal segments is in a planar orientation when the plurality of seal segments is in the unfolded configuration.

10. The access assembly of claim 1, where the connector flexibly couples each segment of the plurality of segments to at least one other segment of the plurality of segments thereby facilitating transitioning the seal assembly between the unfolded configuration and the folded configuration.

11. A seal assembly for an instrument valve assembly, the seal assembly comprising:
a plurality of seal segments transitionable from an unfolded configuration defined by a planar orientation of the plurality of seal segments to a folded configuration defining a substantially hexagonal body, each seal segment of the plurality of seal segments attached to at least one other seal segment of the plurality of seal segments by a connector and each seal segment of the plurality of seal segments includes a base portion and a seal portion extending from the base portion, each of the base portions including an outer edge formed of three segments, wherein each seal segment of the plurality of seal segments is disposed relative to an adjacent seal segment of the plurality of seal segments such that two of the three segments of the outer edge of the respective seal segments align with each other.

12. The seal assembly of claim 11, wherein each seal segment of the plurality of seal segments is rotated sixty degrees (60°) relative to an adjacent seal segment of the plurality of seal segments.

13. The seal assembly of claim 11, wherein the seal portions of the plurality of seal segments taper radially inward.

14. The seal assembly of claim 11, wherein the seal portions of the plurality of seal segments defines an opening.

15. The seal assembly of claim 14, wherein the opening includes a diameter from about 0.025" to about 0.100".

16. The seal assembly of claim 11, wherein the seal portions of the plurality of seal segments form an angle from about 180° to about 275°.

17. The seal assembly of claim 16, wherein the angle is 2100.

18. The seal assembly of claim 11, wherein the plurality of seal segments includes six (6) seal segments.

* * * * *